(12) United States Patent
Bonrath et al.

(10) Patent No.: US 8,426,617 B2
(45) Date of Patent: Apr. 23, 2013

(54) ASYMMETRIC HYDROGENATION OF ALKENES USING CHIRAL IRIDIUM COMPLEXES

(75) Inventors: Werner Bonrath, Freiburg (DE); Frederik Menges, Glienicke (DE); Thomas Netscher, Bad Krozingen (DE); Andreas Pfaltz, Binningen (CH); Bettina Wustenberg, Basel (CH)

(73) Assignee: DSM IP Assets B.V., Heerlen (NL)

( * ) Notice: Subject to any disclaimer, the term of this patent is extended or adjusted under 35 U.S.C. 154(b) by 1309 days.

(21) Appl. No.: 11/793,729

(22) PCT Filed: Dec. 20, 2005

(86) PCT No.: PCT/EP2005/013694
§ 371 (c)(1),
(2), (4) Date: Aug. 8, 2007

(87) PCT Pub. No.: WO2006/066863
PCT Pub. Date: Jun. 29, 2006

(65) Prior Publication Data
US 2008/0039638 A1 Feb. 14, 2008

(30) Foreign Application Priority Data
Dec. 22, 2004 (EP) .................................... 04030432

(51) Int. Cl.
*C07D 311/00* (2006.01)

(52) U.S. Cl.
USPC .......................................... 549/399; 549/398

(58) Field of Classification Search .................. 549/398, 549/399
See application file for complete search history.

(56) References Cited

U.S. PATENT DOCUMENTS

| | | | |
|---|---|---|---|
| 4,925,960 A * | 5/1990 | Lechtken et al. | 549/412 |
| 4,962,242 A | 10/1990 | Yamada et al. | |
| 5,312,939 A | 5/1994 | Hori et al. | |
| 5,488,172 A | 1/1996 | Cereghetti et al. | |
| 5,600,015 A | 2/1997 | Broger et al. | |
| 6,410,755 B1 | 6/2002 | Millis et al. | |
| 6,498,256 B2 | 12/2002 | Pfaltz et al. | |
| 6,759,561 B2 | 7/2004 | Funke et al. | |
| 7,534,921 B2 | 5/2009 | Jäkel et al. | |
| 2001/0047110 A1 | 11/2001 | Kenzo et al. | |

FOREIGN PATENT DOCUMENTS

| | | |
|---|---|---|
| EP | 0 565 975 A2 | 10/1993 |
| EP | 0 806 405 A1 | 11/1997 |
| JP | 03-005492 | 1/1991 |
| JP | 04-074192 | 3/1992 |
| JP | 10-045659 | 2/1998 |
| JP | A 10 045659 | 2/1998 |
| JP | 10-114767 | 5/1998 |
| JP | 10114767 * | 6/1998 |
| JP | 10-251248 | 9/1998 |

OTHER PUBLICATIONS

Frederick Menges et al; "Threonine-Derived Phosphinite-Oxazoline Ligands for the Ir-Catalyzed Enantioselective Hydrogenation"; Advanced Synthesis and Catalysis, 2002, vol. 344, No. 1, pp. 40-44.
Robert H. Crabtree et al; "Directing Effects in Homogeneous Hydrogenation with [Ir(cod)(PCy$_3$)(py)]PF$_6$"; Journal of Organic Chemistry, 1986, vol. 51, pp. 2655-2661.
Guopin Xu et al; "Asymmetric Hydrogenation of Aromatic Olefins Catalyzed by Iridium Complexes of Proline Derived Phosphine-Oxazoline Ligands"; Tetrahedron Letters, 2003, vol. 44, pp. 963-965.
Pfaltz et al, "Iridium-Catalyzed Enantioselective Hydrogenation of Olefins", Advanced Synthesis and Catalysis 2003, 345 (1+2), 33-42.

* cited by examiner

*Primary Examiner* — Taylor Victor Oh
(74) *Attorney, Agent, or Firm* — Nixon & Vanderhye P.C.

(57) ABSTRACT

The invention relates to the (stereoselective) hydrogenation of carbon-carbon double bonds in compounds having at least one such bond, e.g., isoprenoids, non-cyclic sesquiterpenes, tocomonoenols, tocodienols, tocotrienols or derivatives thereof, as well as to the (stereoselective) hydrogenation of parts/extracts of plant oils containing such tocotrienols or derivatives thereof, in the presence of a chiral Ir complex as the catalyst, whereby preferably one stereoisomer is manufactured in an excess.

16 Claims, 5 Drawing Sheets

Case 24498

ASYMMETRIC HYDROGENATION OF ALKENES USING CHIRAL IRIDIUM COMPLEXES

This application is the US national phase of international application PCT/EP2005/013694 filed 20 Dec. 2005 which designated the U.S. and claims benefit of EP 04030432.1, dated 22 Dec. 2004, the entire content of which is hereby incorporated by reference.

The present invention relates to the (stereoselective) hydrogenation of a compound of the formula II with at least one carbon-carbon double bond, especially to the (stereoselective) hydrogenation of isoprenoids, non-cyclic sesquiterpenes, tocomonoenols, tocodienols, tocotrienols or any derivatives thereof, as well as to the (stereoselective) hydrogenation of parts/extracts of plant oils containing such tocotrienols or derivatives thereof, in the presence of a chiral Ir complex as the catalyst, whereby preferably one stereoisomer is manufactured in an excess.

In the prior art there exists no general method for the asymmetric hydrogenation of trisubstituted olefins bearing no functional group in near proximity, that means olefins in which the carbon atoms of the olefinic double bond are spaced from the functional group(s) by two or more $CH_2$-groups could not be stereoselective hydrogenated so far. A "functional group" is understood as a group consisting of an aromatic residue or groups containing heteroatoms like O, N, S, P or similar. Examples of corresponding compounds which are useful for the synthesis of optically active tocopherols (vitamin E) are tocotrienols, unsaturated isoprenoids like geranylacetone or farnesene acid alkyl esters. Therefore, there is a need to provide catalysts for such stereoselective hydrogenation.

Surprisingly it was found that chiral Ir complexes, especially those containing P—N ligand systems, are suitable for that purpose. Such catalysts were until now only known for the stereoselective hydrogenation of aromatic compounds (see A. Pfaltz et al., Adv. Synth. Catal. 2003, 345 (1+2), 33-43; F. Menges, A. Pfaltz, Adv. Synth. Catal. 2002, 344 (1), 40-44; J. Blankenstein, A. Pfaltz, Angew. Chem. Int. Ed. 2001, 40 (23), 4445-4447; A. Pfaltz, Chimia 2004, 58 (1+2), 49-50).

Thus, one aspect of the invention refers to a process for the manufacture of at least one compound of the formula I

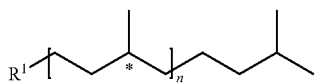

I wherein the position labelled with the asterisk is an asymmetry center and
$R^1$ is selected from the group consisting of linear $C_{1-3}$-alkyl, $C_{5-7}$-cycloalkyl, hydroxyl, hydroxyalkyl (alkyl=$C_{1-4}$-alkyl), oxoalkyl (alkyl=$C_{1-4}$-alkyl), alkylcarbonyl (alkyl=$C_{1-4}$-alkyl), alkoxycarbonyl (alkoxy=linear $C_{1-4}$-alkoxy) and a group of the formula

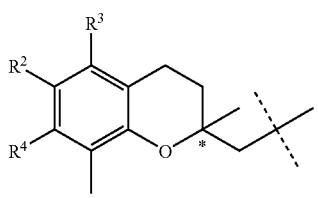

with $R^2$ being a hydroxyl group or a protected hydroxyl group, and $R^3$ and $R^4$ being independently from each other hydrogen or methyl, and n being an integer from 1 to 10, preferably from 1 to 3,
comprising the step of
hydrogenating a compound of the formula II

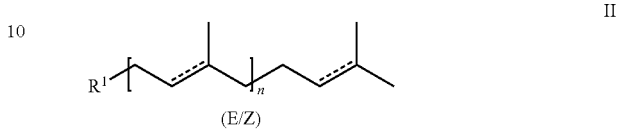

II wherein at least one carbon-carbon double bond is present, and wherein the dotted lines represent the possible positions of such (facultative) carbon-carbon double bonds; and $R^1$ and n are as above,
in the presence of a chiral Ir complex as the catalyst.

Preferably in such process one stereoisomer of the compound I is manufactured in excess. If a compound of formula II with only one prochiral center is used preferably one enantiomer is manufactured in excess. The stereoselectivity of the hydrogenation can be controlled by appropriate choive of the catalyst.

Starting Material

Examples of the compounds of the formula II are those presented in FIG. 4:
IIa1=(E)-Dihydrogeranylacetone, IIa2=(Z)-dihydronerylacetone, IIa3=(E)-geranylacetone, IIa4=(Z)-nerylacetone, IIb=(all-E)-farnesol; IIc=(all-E)-farnesene acid ethyl ester, (S)-XII=(2S,3'E,7'E)-tocotrienol and derivatives thereof, (R)-XII=(2R,3'E,7'E)-tocotrienol and derivatives thereof, (S)-XIII=(2S,3'E,7'E)-tocomono- and -dienols with the dotted lines indicating the possible positions of the one or two double bond(s), (R)-XIII=(2R,3'E,7'E)-tocomono- and -dienols with the dotted lines indicating the possible positions of the one or two double bond(s).

| | Formula (S)-XII | Formula (R)-XII |
|---|---|---|
| $R^3 = R^4$ = methyl; $R^2$ = (protected) hydroxyl group | (2S,3'E,7'E)-α-tocotrienol and derivative thereof | (2R,3'E,7'E)-α-tocotrienol and derivative thereof |
| $R^3 = R^4$ = methyl; $R^2$ = acetyloxy | (2S,3'E,7'E)-α-tocotrienyl acetate | (2R,3'E,7'E)-α-tocotrienyl acetate |
| $R^3$ = methyl; $R^4$ = H; $R^2$ = (protected) hydroxyl group | (2S,3'E,7'E)-β-tocotrienol and derivative thereof | (2R,3'E,7'E)-β-tocotrienol and derivative thereof |
| $R^3$ = methyl; $R^4$ = H; $R^2$ = acetyloxy | (2S,3'E,7'E)-β-tocotrienyl acetate | (2R,3'E,7'E)-β-tocotrienyl acetate |
| $R^3$ = H, $R^4$ = methyl; $R^2$ = (protected) hydroxyl group | (2S,3'E,7'E)-γ-tocotrienol and derivative thereof | (2R,3'E,7'E)-γ-tocotrienol and derivative thereof |
| $R^3$ = H, $R^4$ = methyl; $R^2$ = acetyloxy | (2S,3'E,7'E)-γ-tocotrienyl acetate | (2R,3'E,7'E)-γ-tocotrienyl acetate |
| $R^3 = R^4$ = H; $R^2$ = (protected) hydroxyl group | (2S,3'E,7'E)-δ-tocotrienol and derivative thereof | (2R,3'E,7'E)-δ-tocotrienol and derivative thereof |
| $R^3 = R^4$ = H; $R^2$ = acetyloxy | (2S,3'E,7'E)-δ-tocotrienyl acetate | (2R,3'E,7'E)-δ-tocotrienyl acetate |

Preferably the compound of the formula II is an isoprenoid, a non-cyclic sesquiterpene, a tocomonoenol, a tocodienol or a tocotrienol.

An isoprenoid is an oligo(isoprene) or a poly(isoprene) and derivatives thereof which contain at least one carbon-carbon double bond. Preferably the carbon-carbon double bond has the E configuration.

The tocomonoenol, the tocodienol and/or the tocotrienol is of the formula XIII,

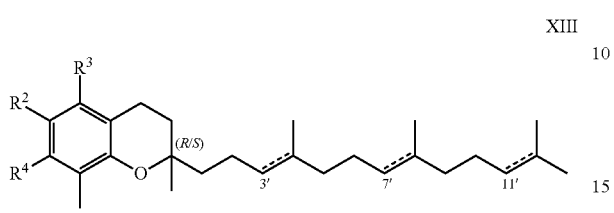

XIII wherein the dotted bonds are optional and at least one of the dotted bonds is present,
and wherein $R^2$ is a hydroxyl group or a protected hydroxyl group and $R^3$ and $R^4$ are independently from each other hydrogen or methyl.

Compound XIII thus encompasses (3'E)-tocomonoenols, (7'E)-tocomonoenols, (11')-tocomonoenols, (3'E,7'E)-tocodienols, (3'E,11')-tocodienols, (7'E,11')-tocodienols, as well as (3'E,7'E)-tocotrienols.

Concerning the Substituent $R^2$ in Formulae I, II and XIII:

$R^2$ is a hydroxyl group or a protected hydroxyl group. The hydroxyl group can be protected as ether, ester, or acetal.

Examples of ethers and acetals are the methylether, the methoxymethylether, the methoxyethylether and the tetrahydropyranyl ether, as well as compounds where $R^2$ is ethoxyethyl or methoxyethoxyethyl.

Examples of esters are the acetic acid ester and esters with other carbonic acids such as formic acid ester, succinic acid monoester (or derivatives), propionic acid ester, benzoic acid ester and palmitic acid ester.

Preferably $R^2$ is a protected hydroxyl group, whereby the hydroxyl group is protected as ether or ester, more preferably as ester, especially preferably $R^2$ is acetyloxy.

In another aspect the present invention is also concerned with a process for the manufacture of a hydrogenated part or extract of a plant oil, preferably of palm oil, comprising the step of hydrogenating the part or extract of the plant oil comprising at least a tocotrienol or derivative thereof in the presence of a chiral Ir complex as the catalyst. That means in the present invention such "a part or extract of the plant oil comprising at least a tocotrienol or derivative thereof" is also encompassed by the term "compound of the formula II with at least one carbon-carbon double bond".

The expression "part of a plant oil" encompasses any untreated or treated part of the plant oil, any concentrated part as well as the whole plant oil itself. "treated" means chemically treated such as distilled or extracted or thermally treated.

Preferably the edible plant oil is treated in such a way that a part is obtained where the tocotrienols originally contained in the edible plant oil are enriched ("concentrate"). This part of the edible plant oil can be per se not edible.

Examples of plant oils are any edible plant oils known to the person skilled in the art. Especially preferred is palm oil which contains beside small amounts of α- and γ-tocopherol large amounts of tocotrienols.

In a preferred embodiment of the invention the tocotrienol or the derivative thereof is hydrogenated to a tocopherol (derivative), preferably to a highly stereoisomerically enriched (all-R)-tocopherol (derivative).

Catalyst

Suitable catalyst for the process of the present invention are Ir complexes with chiral organic ligands, especially those disclosed by A. Pfaltz et al. in Adv. Synth. Catal. 2003, 345 (1+2), 33-43; by F. Menges and A. Pfaltz in Adv. Synth. Catal. 2002, 344 (1), 40-44; by J. Blankenstein and A. Pfaltz in Angew. Chem. Int. Ed. 2001, 40 (23), 4445-4447, by A. Pfaltz in Chimia 2004, 58 (1+2), 49-50 and in U.S. Pat. No. 6,632,954.

Suitable catalysts are especially the Ir complexes of the formula III, IV, V, VI, VII, VIII, IX, X, XI or XV and their enantiomers

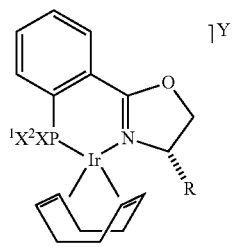

III

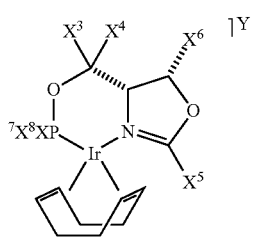

IV

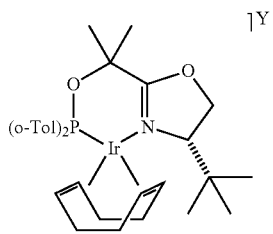

V

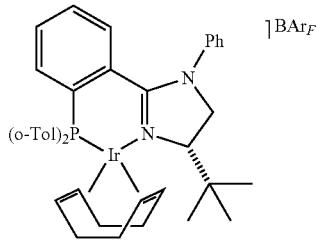

VI

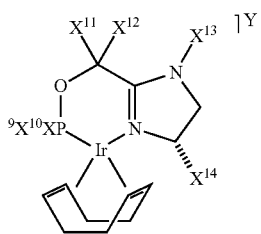

VII

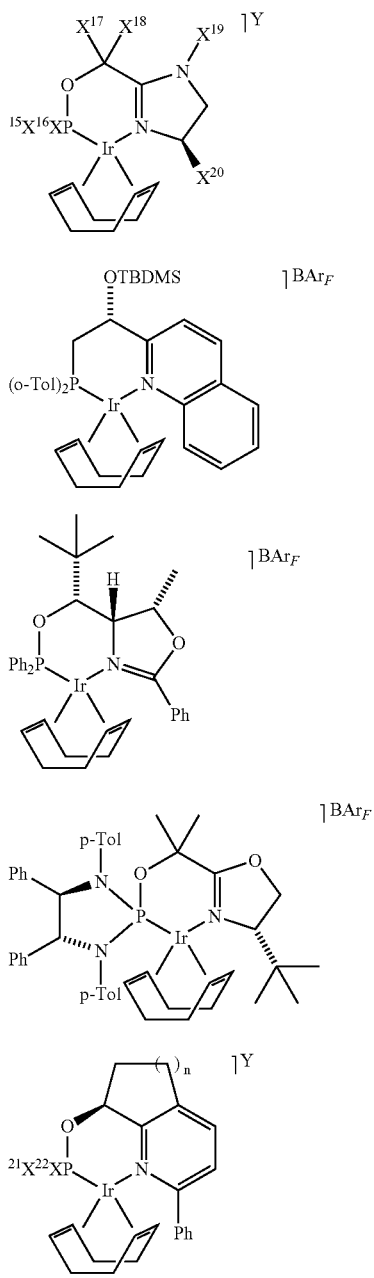

wherein R, $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$, $X^{17}$, $X^{18}$, $X^{19}$, $X^{20}$, $X^{21}$ and $X^{22}$ are independently from each other hydrogen, $C_{1-4}$-alkyl, $C_{5-7}$-cycloalkyl, phenyl (optionally substituted with one to three $C_{1-4}$-alkyl, $C_{1-4}$-alkoxy and/or $C_{1-4}$-perfluoroalkyl groups), benzyl, 1-naphthyl, or ferrocenyl, the anion Y is a low coordinating anion, n is 1 or 2, and wherein "o-Tol" means ortho-tolyl, "Ph" means phenyl, "TBDMS" means tert-butyl-di-methylsilyl, "p-Tol" means para-tolyl, and "$BAr_F$" means tetra(3,5-bis(trifluoromethyl)phenyl)borate.

Suitable catalysts are also the corresponding Ir complexes and their enantiomers, in which the cyclooctadiene ligand is replaced by olefins, e.g. ethene, norbornadiene.

Preferred chiral Ir complexes suitable for the process of the present invention are Ir complexes of the formulae III to XI, wherein R, $X^1$, $X^2$, $X^3$, $X^3$, $X^5$, $X^6$, $X^7$, $X^8$, $X^9$, $X^{10}$, $X^{11}$, $X^{12}$, $X^{13}$, $X^{14}$, $X^{15}$, $X^{16}$, $X^{17}$, $X^{18}$, $X^{19}$, $X^{20}$, $X^{21}$ and $X^{22}$ are independently from each other hydrogen, $C_{1-4}$-alkyl, $C_{5-7}$-cycloalkyl, phenyl (optionally substituted with one to three $C_{1-4}$-alkyl, $C_{1-4}$-alkoxy and/or $C_{1-4}$-perfluoroalkyl groups), benzyl, 1-naphthyl, or ferrocenyl, and the anion Y is a weakly coordinating anion such as $PF_6^-$, $SbF_6^-$, $BAr_F^-$, $BF_4^-$, $F_3C-SO_3^-$, $ClO_4^-$, tetra(perfluoroaryl)borate or tetra(perfluoroalkyloxy)aluminate whereby the perfluoroaryl is a phenyl substituted with 1 to 5 perfluoro-$C_{1-4}$-alkyl groups and the perfluoroalkyloxy has 1 to 4 carbon atoms.

Especially preferred are Ir complexes of the formulae III to XI and XV, wherein

R, $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$, $X^{17}$, $X^{18}$, $X^{19}$, $X^{20}$, $X^{21}$ and $X^{22}$ are independently from each other hydrogen, methyl, ethyl, iso-propyl, n-butyl, iso-butyl, tert-butyl, cyclohexyl, phenyl, benzyl, o-tolyl, m-tolyl, 4-methoxyphenyl, 4-trifluoromethylphenyl, 3,5-di-tert-butylphenyl, 3,5-dimethoxyphenyl, 1-naphthyl, or ferrocenyl, and the anion Y is tetra(perfluoroaryl)borate or tetra(perfluoroalkyloxy)aluminate whereby the perfluoroaryl is a phenyl substituted with 1 to 3 perfluoro-$C_{1-4}$-alkyl groups and the perfluoroalkyloxy has 1 to 4 carbon atoms.

More preferred chiral Ir complexes suitable for the process of the present invention are Ir complexes of the formulae III to XI, and XV, wherein R, $X^5$, $X^{14}$ and $X^{20}$, $X^{21}$, and $X^{22}$ are independently from each other hydrogen, iso-propyl, tert-butyl, phenyl, 3,5-di-tert-butylphenyl or ferrocenyl, $X^1$ and $X^2$, as well as $X^7$ and $X^8$, as well as $X^9$ and $X^{10}$ and $X^{15}$ and $X^{16}$ are independently from each other phenyl, o-tolyl, cyclohexyl or iso-propyl, preferably $X^1$ and $X^2$ as well as $X^7$ and $X^8$ or $X^9$ and $X^{10}$ or $X^{15}$ and $X^{16}$ are the same, $X^3$ and X4 as well as $X^{11}$ and $X^{12}$ as well as $X^{17}$ and $X^{18}$ are independently from each other methyl, ethyl, n-butyl, iso-butyl or benzyl, preferably $X^3$ and $X^4$, $X^{11}$ and $X^{12}$, $X^{17}$ and $X^{18}$ are the same, $X^6$ is hydrogen or methyl, $X^{13}$ and $X^{19}$ are independently from each other phenyl, cyclohexyl, 4-methoxyphenyl, 3,5-dimethoxyphenyl, 4-trifluoromethylphenyl, benzyl, m-tolyl or 1-naphthyl, Y is tetra(3,5-bis(trifluoromethyl)phenyl)borate [B(3,5-$C_6H_3(CF_3)_2)_4$]$^-$ or tetra(perfluorotert-butyloxy)aluminate [Al(OC(CF$_3$)$_3$)$_4$]$^-$ and n is as defined earlier.

Even more preferred chiral Ir complexes suitable for the process of the present invention are Ir complexes of the formulae III to XI, and XV, wherein R is hydrogen, iso-propyl or tert-butyl, $X^1$ and $X^2$ are independently from each other phenyl, o-tolyl, cyclohexyl or iso-propyl, preferably $X^1$ and $X^2$ are the same, $X^3$ and $X^4$ are independently from each other benzyl or iso-butyl, preferably $X^3$ and $X^4$ are the same, $X^5$ is phenyl, 3,5-di-tert-butylphenyl or ferrocenyl, $X^6$ is hydrogen or methyl, $X^7$ and $X^8$ are independently from each other phenyl or cyclohexyl, preferably $X^7$ and $X^8$ are the same, $X^9$ and $X^{10}$ are independently from each other phenyl or o-tolyl, preferably $X^9$ and $X^{10}$ are the same, $X^{11}$ and $X^{12}$ are independently from each other methyl, ethyl or n-butyl, preferably $X^{11}$ and $X^{12}$ are the same, $X^{13}$ is phenyl, cyclohexyl, 4-methoxyphenyl, 3,5-dimethoxyphenyl, 4-trifluoromethylphenyl, benzyl, m-tolyl or 1-naphthyl, $X^{14}$ is iso-propyl or tert-butyl, $X^{15}$ and $X^{16}$ are independently from each other phenyl or o-tolyl, preferably $X^{15}$ and $X^{16}$ are the same, $X^{17}$ and $X^{18}$ are independently from each other methyl or n-butyl, preferably $X^{17}$ and $X^{18}$ are the same, $X^{19}$ is phenyl or 1-naphthyl, $X^{20}$ is iso-propyl or tert-butyl, $X^{21}$ and $X^{22}$ are Y is tetra(3,5-bis(trifluoromethyl)phenyl)borate $[B(3,5-C_6H_3(CF_3)_2)_4]^-$ or tetraperfluorotert-butyloxyaluminate $[Al(OC(CF_3)_3)_4]^-$ and n is as defined earlier.

The most preferred chiral Ir complexes suitable for the process of the present invention are the Ir complexes of the formulae III to XI presented in the FIG. 1 to 3. Hereby the following abbreviations are used in the formulae:

"Cy"=cyclohexyl, "Bn"=benzyl, "i-Bu"=iso-butyl, "n-Bu"=n-butyl, "t-Bu"=tert-butyl, "Fc"=ferrocenyl, "o-Tol"=o-tolyl, "p-Tol"=p-tolyl, "i-Pr"=iso-propyl, "Me"=methyl, "Ph"=phenyl, "TBDMS"=tert-butyl-dimethyl silyl, "BAr$_F$" is tetra(3,5-bis(trifluoromethyl)phenyl)borate $[B(3,5-C_6H_3(CF_3)_2)_4]^-$.

Reaction Conditions

Figure 1:
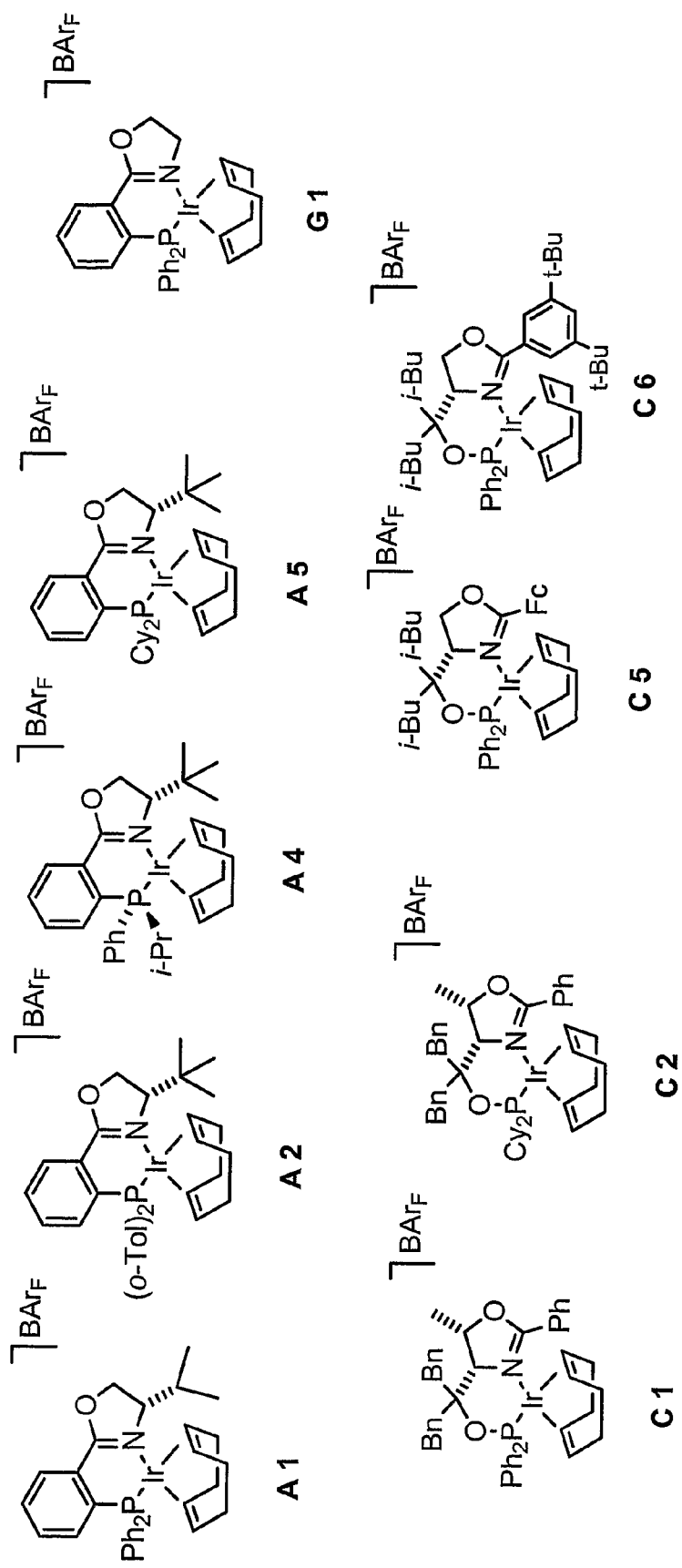
FIG. 1 shows preferred Ir complexes of the formula III (A1, A2, A4, A5, G1) and IV (C1, C2, C5, C6).

In the hydrogenation process of the present invention the amount of the catalyst is conveniently from about 0.05 to about 5 mol %, preferably from about 0.09 to about 2.5 mol %, more preferably from about 0.1 to about 2.0 mol-%, based on the amount of the compound of the formula II.

Preferred examples of halogenated aliphatic hydrocarbons are mono- or polyhalogenated linear, branched or cyclic $C_1$- to $C_{15}$-alkanes. Especially preferred examples are mono- or polychlorinated or -brominated linear, branched or cyclic $C_1$- to $C_{15}$-alkanes. More preferred are mono- or polychlorinated linear, branched or cyclic to $C_1$- to $C_{15}$-alkanes. Most preferred are dichloromethane, 1,2-dichloroethane, toluene 1,1, 1-trichloroethane, chloroform, and methylene bromide. Further, toluene, benzene, and chlorobenzene come into consideration.

The reaction may be carried out under solvent free conditions, or in presence of one or more of the solvents mentioned above. The concentration of the reactants in the solution is not critical.

The reaction is conveniently carried out at an absolute pressure of hydrogen from about 1 to about 100 bar, preferably at an absolute pressure of hydrogen from about 20 to about 75 bar. The reaction temperature is conveniently between about 0 to about 100° C., preferably between about 10 to about 40° C.

The sequence of addition of the reactants and solvent is not critical.

PREFERRED EMBODIMENTS OF THE INVENTION

In a first preferred embodiment of the present invention, (Z)-nerylacetone or (E)-geranylacetone or any mixture thereof is hydrogenated in the presence of a chiral Ir complex selected from the group consisting of catalyst A2 (see FIG. 1), D1 (see FIG. 3), B1 (see FIG. 3) and E1 (see FIG. 2), preferably in the presence of a chiral Ir complex selected from the group consisting of catalyst D1, B1 and E1, more preferably in the presence of a chiral Ir complex selected from the group consisting of catalyst B1 and E1 to form a mixture of the enantiomers (6S)-6,10-dimethylundecane-2-one and (6R)-6, 10-dimethylundecane-2-one. Preferably the hydrogenation is stereoselective in that way that one enantiomer is present in the mixture in an enantiomeric excess, preferably of at least 84%, more preferably of at least 90%.

In a second preferred embodiment of the present invention (E)-farnesol is hydrogenated in the presence of the chiral Ir complex E1 (see FIG. 2) or B1 (see FIG. 3) to form a mixture of two enantiomeric pairs (3R,7S)-3,7,11-trimethyldodecane-1-ol and (3S,7R)-3,7,11-trimethyldodecane-1-ol as well as (3R,7R)-3,7,11-trimethyldodecane-1-ol and (3S,7S)-3,7,11-trimethyldodecane-1-ol. Hereby preferably the stereoisomer (3S,7S)-3,7,11-trimethyldodecane-1-ol is present in the mixture obtained after the hydrogenation in an excess compared to the other stereoisomers, preferably in an amount of at least 70%, more preferably in an amount of at least 75%.

In a third preferred embodiment of the present invention (E)-farnesene acid ethyl ester is hydrogenated in the presence of the chiral Ir complex B1 (see FIG. 3) or E1 (see FIG. 2) to form a mixture of two enantiomeric pairs (3R,7S)-3,7,11-trimethyldodecanoic acid ethyl ester and (3S,7R)-3,7,11-trimethyldodecanoic acid ethyl ester as well as (3R,7R)-3,7,11-trimethyldodecanoic acid ethyl ester and (3S,7S)-3,7,11-trimethyldodecanoic acid ethyl ester. Hereby the hydrogenation is preferably stereoselective in that way that the stereoisomer (3S,7S)-3,7,11-trimethyldodecanoic acid ethyl ester is manufactured—compared to the other stereoisomers—in an excess, preferably in an amount of at least 55%, more preferably in an amount of at least 70%.

In a fourth preferred embodiment of the present invention (2R,3'E,7'E)-α-tocotrienyl acetate is hydrogenated in the presence of the chiral Ir complex E1 (see FIG. 2), E2 (see FIG. 3), E7 (see FIG. 2) or E15 (see FIG. 3) to form a mixture of the four diastereoisomers (2R,4'S,8'R)-α-tocopheryl acetate, (2R,4'R,8'S)-α-tocopheryl acetate, (2R,4'R,8'R)-α-tocopheryl acetate and (2R,4'S,8'S)-α-tocopheryl acetate, wherein one diastereoisomer is manufactured in an excess.

When the chiral Ir complex E2 or E15 (see FIG. 3) is used as the catalyst, the stereoisomer (2R,4'R,8'R)-α-tocopheryl acetate—compared to the other diastereoisomers—is manufactured in an excess, preferably in an amount of at least 55%, more preferably in an amount of at least 90%.

In a fifth preferred embodiment of the present invention (2S,3'E,7'E)-α-tocotrienyl acetate is hydrogenated in the presence of a chiral Ir complex selected from the group consisting of E3, E4, E6, E8, E9, E10, E11, E12, E13, E14 (all FIG. 2) as the catalyst, preferably in the presence of the chiral Ir complex E13 or E14 as the catalyst, to form a mixture of the four diastereoisomers (2S,4'S,8'R)-α-tocopheryl acetate, (2S,4'R,8'S)-α-tocopheryl acetate, (2S,4'R,8'R)-α-tocopheryl acetate and (2S,4'S,8'S)-α-tocopheryl acetate, whereby one diastereoisomer is manufactured in an excess. Preferably the diastereoisomer (2S,4'S,8'S)-α-tocopheryl acetate is manufactured in an excess—compared to the other diastereoisomers, preferably in an amount of at least 65%, more preferably in an amount of at least 85%.

In a sixth preferred embodiment of the present invention (2R,3'E,7'E)-γ-tocotrienyl acetate is hydrogenated in the presence of the chiral Ir complex C1 (see FIG. 1), D1 (see FIG. 3), E1 (see FIG. 2) or F1 (see FIG. 3) as the catalyst, to form a mixture of the four diastereoisomers (2R,4'S,8'R)-γ-tocopheryl acetate, (2R,4'R,8'S)-γ-tocopheryl acetate, (2R, 4'R,8'R)-γ-tocopheryl acetate and (2R,4'S,8'S)-γ-tocopheryl acetate whereby one diastereoisomer is manufactured in an excess. When the chiral Ir complex F1 is used as the catalyst, the diastereoisomer (2R,4'R,8'R)-α-tocopheryl acetate is manufactured in an excess—compared to the other diastereoisomers, preferably in an amount of at least 45%.

Particular catalysts for use in the present invention are the chiral complexes represented by the formulae E1 to E15.

Finally the present invention is also directed to the use of a chiral Ir complex, especially one of the formulae III to XI as described above, as catalyst for the (stereoselective) hydrogenation of a compound selected from the group consisting of isoprenoids, non-cyclic sesquiterpenes, tocomonoenols, tocodienols and tocotrienols.

FIGS. 1 to 5

FIG. 1 shows preferred Ir complexes of the formula III (A1, A2, A4, A5, G1) and IV (C1, C2, C5, C6).

Figure 2:
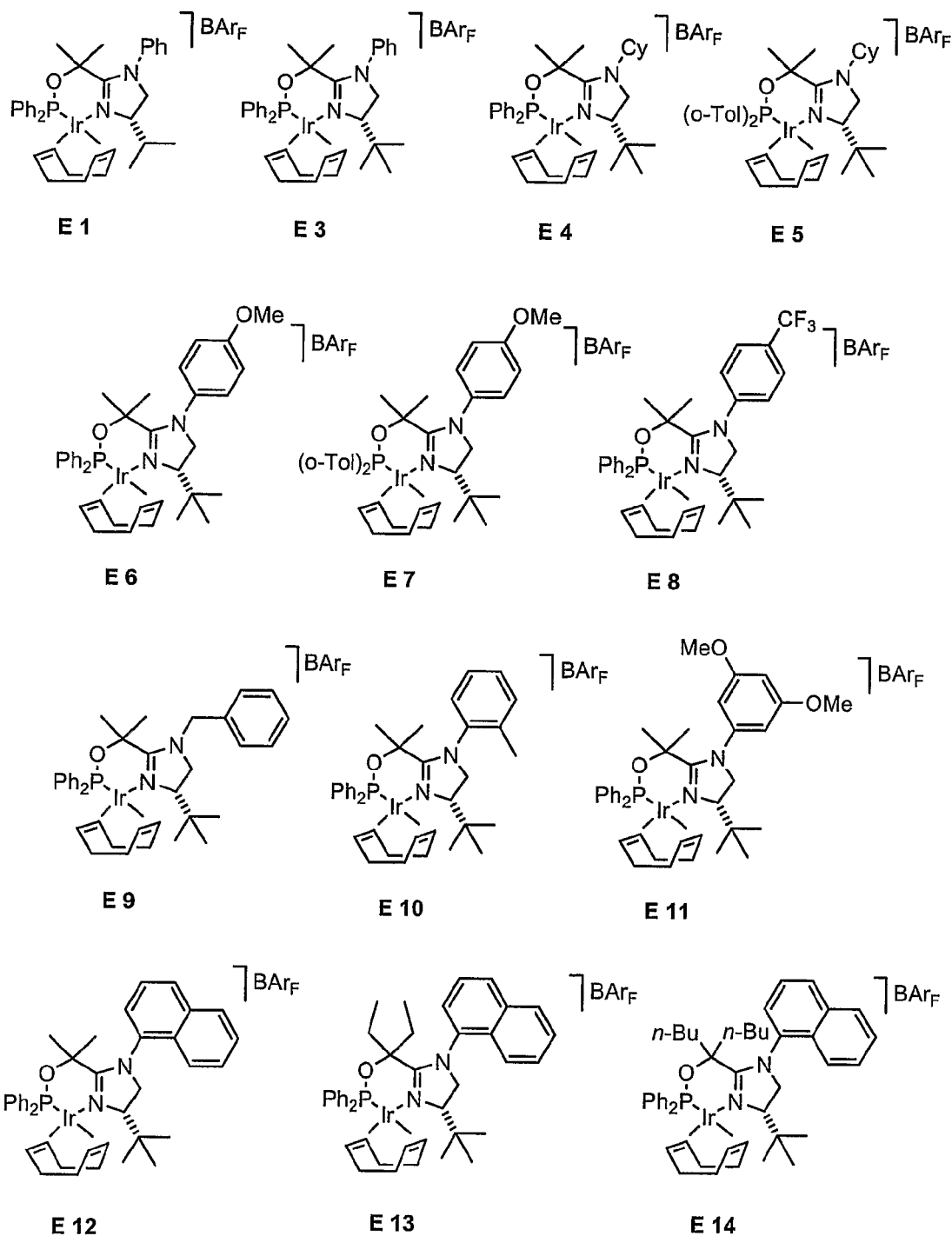
FIG. 2 shows preferred Ir complexes of the formulae VII (E1 and E3 to E14).

FIG. 2 shows preferred Ir complexes of the formulae VII (E1 and E3 to E14).

Figure 3:
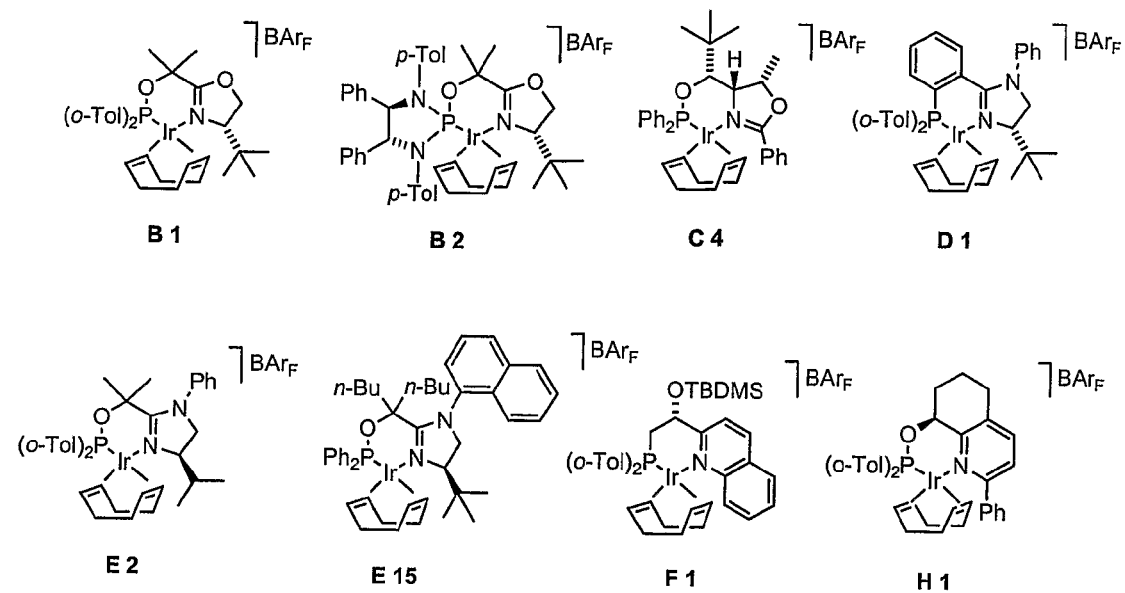
FIG. 3 shows the Ir complexes of the formulae V (B1), VI (D1), VIII (E2, E15), IX (F1), X (C4), XI (B2) and XV (H1).

FIG. 3 shows the Ir complexes of the formulae V (B1), VI (D1), VIII (E2, E15), IX (F1), X (C4) and XI (B2).

Figure 4:
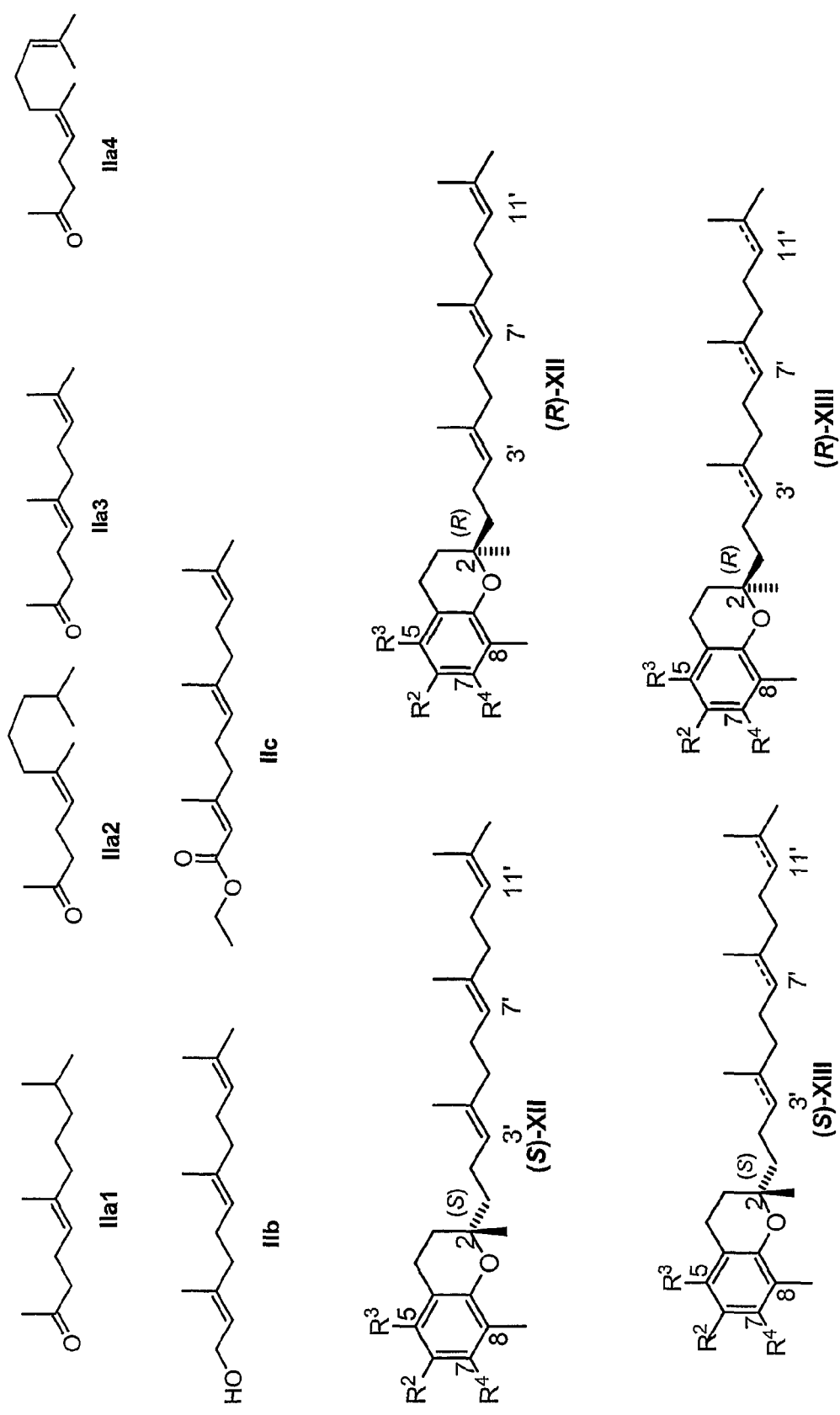

FIG. 4 shows examples of starting materials: IIa1=(E)-Dihydrogeranylacetone, IIa2=(Z)-dihydronerylacetone, IIa3=(E)-geranylacetone, IIa4=(Z)-nerylacetone, IIb=(all-E)-farnesol; IIc=(all-E)-farnesene acid ethyl ester, (S)-XII=(2S,3'E,7'E)-tocotrienol and derivatives thereof, (R)-XII=(2R,3'E,7'E)-tocotrienol and derivatives thereof, (S)-XIII=(2S,3'E,7'E)-tocomono- and -dienols with the dotted lines indicating the possible positions of the one or two double bond(s), (R)-XIII=(2R,3'E,7'E)-tocomono- and -dienols with the dotted lines indicating the possible positions of the one or two double bond(s).

Figure 5:
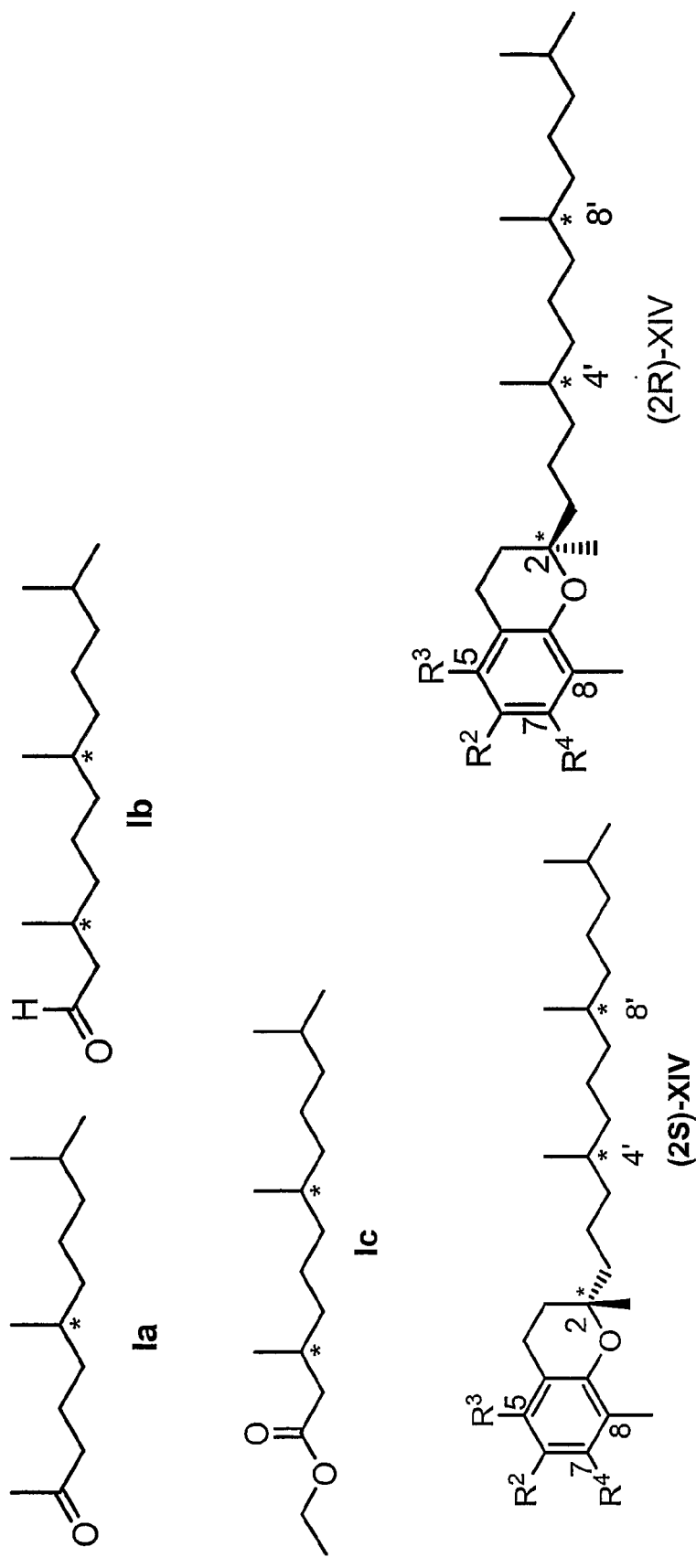

FIG. 5 shows examples of products of the process of the present invention, whereby the asterisks indicate chirality centers: Ia=6,10-dimethylundecane-2-one, Ib=3,7,11-trimethyldodecane-1-ol, Ic=3,7,11-trimethyldodecane acid ethyl ester, (2S)—XIV=(2S)-tocopherol and derivatives thereof, (R)-XIV=(2R)-tocopherol and derivatives thereof.

|  | Formula (2S)-XIV | Formula (2R)-XIV |
|---|---|---|
| $R^3 = R^4$ = methyl; $R^2$ = (protected) hydroxyl group | (2S)-α-tocopherol and derivative thereof | (2R)-α-tocopherol and derivative thereof. |
| $R^3 = R^4$ = methyl; $R^2$ = acetyloxy | (2S)-α-tocopheryl acetate | (2R)-α-tocopheryl acetate |
| $R^3$ = methyl; $R^4$ = H; $R^2$ = (protected) hydroxyl group | (2S)-β-tocopherol and derivative thereof | (2R)-β-tocopherol and derivative thereof |
| $R^3$ = methyl; $R^4$ = H; $R^2$ = | (2S)-β-tocopheryl acetate | (2R)-β-tocopheryl acetate |
| $R^3$ = H, $R^4$ = methyl; $R^2$ = (protected) hydroxyl group | (2S)-γ-tocopherol and derivative thereof | (2R)-γ-tocopherol and derivative thereof |
| $R^3$ = H, $R^4$ = methyl; $R^2$ = acetyloxy | (2S)-γ-tocopheryl acetate | (2R)-γ-tocopheryl acetate |
| $R^3 = R^4$ = H; $R^2$ = (protected) hydroxyl group | (2S)-δ-tocopherol and derivative thereof | (2R)-δ-tocopherol and derivative thereof |
| $R^3 = R^4$ = H; $R^2$ = acetyloxy | (2S)-δ-tocopheryl acetate | (2R)-δ-tocopheryl acetate |

The invention is illustrated further by the following examples.

EXAMPLES

The following abbreviations are used:
"TLC"=thin layer chromatography; "GC"=gas chromatography; "GC-MS"=gas chromatography—mass spectrometry; "HPLC"=high pressure/performance liquid chromatography.

The asterisks in the $^{13}C/^1H$-NMR parts mean that the signs could not be assigned unambiguously to a carbon/proton and the ones labelled with the asterisks are interchangeable.

The enantiomeric excess concerning the R-enantiomer is calculated as follows
[(amount of R-enantiomer minus amount of S-enantiomer)/(amount of R-enantiomer plus amount of S-enantiomer)]×100.

The enantiomeric excess concerning the R-enantiomer is calculated as follows

[(amount of R-enantiomer minus amount of S-enantiomer)/(amount of R-enantiomer plus amount of S-enantiomer)]×100.

General Remarks

All starting materials were prepared by DSM Nutritional Products, Lalden/Sisseln, Switzerland: (E)-Geranylacetone, 99.2% (GC); (Z)-nerylacetone, 97.6% (GC); (E)-dihydrogeranylacetone, 99.2% (GC); (Z)-dihydronerylacetone, 98.9% (GC); (all-E)-farnesol, 97.7% (GC); (2E,6E)-farnesene acid ethyl ester, 99.0% (GC); (2E,6Z)-farnesene acid ethyl ester, 78.2% (GC), contains 1.4% of the (6E) isomer and 17.6% of another not known isomer (GC-MS); (R,E,E)-alpha-tocotrienol acetate, ca. 99%; (S,E,E)-alpha-tocotrienyl acetate, ca. 99%; (R,E,E)-gamma-tocotrienyl acetate (prepared by total synthesis) 99.7% (HPLC); (S,E,E)-gamma-tocotrienyl acetate (prepared by total synthesis), 99.8% (HPLC). Reference compounds: (all-rac)-alpha-Tocopherol, 99.6% (GC); (all-rac)-alpha-tocopheryl acetate, 97.7% (GC); (all-rac)-alpha-tocopheryl methyl ether, 97.8% (GC); (all-rac)-gamma-tocopherol, 96.8% (GC); (R,R,R)-gamma-tocopheryl acetate, ca. 99% (GC); (all-rac)-gamma-tocopheryl methyl ether, 97.9% (GC).

If not stated otherwise, the GC analyses were performed with an Agilent 6890 GC FID on a CP-Sil-88 (Chrompack, Netherlands) 50 m×0.25 mm column. The carrier gas was hydrogen with 90 kPa. The samples were injected as 0.3% solutions in dichloromethane with a split ratio of 1/30. The injector was held at 250° C. whereas the oven temperature was programmed from 110-200° C. at 0.5° C./min, the detector was at 250° C.

In case of complete conversion a derivative of the hydrogenated product was prepared to determine the distribution of the stereoisomers.

Hydrogenated ketones or aldehydes e.g. were reacted with L- or D-trimethylsilyl diisopropyltartrat (shortly "L-3", or "D-3") in the presence of trimethylsilyl triflate [$Si(CH_3)_3(OSO_2CF_3)$] to the diastereomeric ketals and acetals, respectively. With the aid of achiral gas chromatography the ratio of the diastereomers could be determined and thus the selectivity of the stereoselective hydrogenation determined indirectly. (See also A. Knierzinger, W. Walther, B. Weber, T. Netscher, Chimia 1989, 43, 163-164; A. Knierzinger, W. Walther, B. Weber, R. K. Müller, T. Netscher, Helvetica Chimica Acta 1990, 73, 1087-1107)

For the determination of the ratio of the diastereoisomers of the prepared tocopheryl acetates these were first reduced to the corresponding tocopherols with LiAlH$_4$ and then reacted with dimethyl sulphate to the tocopheryl methyl ethers. There were obtained four diastereoisomers. Their ratio was determined via achiral gas chromatography. (See also W. Walther, T. Netscher, Chirality 1996, 8, 397-401.)

The stereoisomeric composition of tocopherols (methyl ether derivatives) was also checked by chiral HPLC (Chiracel OD, 250×4.6 mm, solvent n-hexane, detection at 220 nm) in the case of the 2-(R)-isomers.

If examples were carried out at "room temperature", this indicates that the reaction was carried out at a temperature of from about 20° C. to about 30° C.

Procedure 1

In an autoclave 0.25 mmol of the substrate, 1 mol-% of the Ir complex and 1.25 ml of absolute dichloromethane were put. The autoclave was closed and a pressure of 50 bar of hydrogen was applied. Under stirring the reaction solution was kept at room temperature for two hours. Afterwards the pressure was released and the solvent removed. For determining the conversion the raw product was analysed by GC without any further purification. If the reaction was complete, the product was converted into a derivative which enabled the determination of the stereoisomeric composition as illustrated further below in more detail, e.g., by converting a ketone to the (+)-L-diisopropyltartrate acetal and the (−)-D-diisopropyltartrate acetal, respectively.

Examples 1 to 25

Preparation of 6,10-Dimethylundecan-2-on

The hydrogenation was carried out according to procedure 1, whereby 0.25 mmol of the substrate and 1 mol-% of the Ir-catalyst were used. The following substrates were used:

(E)-Dihydrogeranylacetone [=(E)-6,10-dimethylundec-5-ene-2-one] (49.1 mg), (Z)-dihydronerylacetone [=(Z)-6,10-dimethylundec-5-ene-2-one] (49.1 mg), (E)-geranylacetone [=(E)-6,10-dimethylundeca-5,9-diene-2-one] (48.6 mg) or (Z)-nerylacetone [=(Z)-6,10-dimethylundeca-5,9-dien-2-on] (48.6 mg).

$^1$H-NMR (400.1 MHz, CDCl$_3$) of the product: δ=0.85 (d, $^3$J=6.6 Hz, 3 H, —CH(CH$_3$)—), 0.86 (d, $^3$J=6.6 Hz, 6 H, —CH(CH$_3$)$_2$), 1.10 (m, 4 H, 2 CH$_2$), 1.26 (m, 4 H, 2 CH$_2$), 1.39 (m, 1 H, CH), 1.54 (m, 3 H, CH$_2$, CH), 2.13 (s, 3 H, —C(O)—CH$_3$), 2.40 (t, 3J=7.6 Hz, 2 H, —C(O)—CH$_2$—) .—GC: Optima 5-Amin, 100 kPa He, temperature program: 100° C. (3 min), 2° C./min, 155° C. (O), 20° C./min, 250° C. (5 min); solvent: n-heptane; $t_R$ [Ia]=27.3 min, $t_R$ [IIa1]=28.1 min, $t_R$ [IIa2]=27.0 min, $t_R$ [IIa3]=30.3 min, $t_R$ [IIa4]=29.2 min.

The results are presented in the following tables 1 to 6:

TABLE 1

Hydrogenation of (E)-dihydrogeranylacetone in dichloromethane

| Example | Catalyst | Conversion [%] | Enantiomeric excess [%] |
|---|---|---|---|
| 1 | A 1 | >99 | 40 (S) |
| 2 | A 2 | >99 | 87 (S) |
| 3 | C 1 | >99 | 45 (S) |

TABLE 2

Hydrogenation of (E)-geranylacetone in dichloromethane

| Example | Catalyst | Conversion [%] | Enantiomeric excess [%] |
|---|---|---|---|
| 4 | A 1 | >99 | 45 (S) |
| 5 | A 2 | >99 | 87 (S) |
| 6 | C 1 | >99 | 50 (S) |

TABLE 3

Hydrogenation of (Z)-dihydronerylacetone in dichloromethane

| Example | Catalyst | Conversion [%] | Enantiomeric excess [%] |
|---|---|---|---|
| 7 | A 1 | >99 | 41 (R) |
| 8 | A 2 | >99 | 85 (R) |
| 9 | C 1 | >99 | 51 (R) |

TABLE 4

Hydrogenation of (Z)-nerylacetone in dichloromethane

| Example | Catalyst | Conversion [%] | Enantiomeric excess [%] |
|---|---|---|---|
| 10 | A 1 | >99 | 37 (R) |
| 11 | A 2 | >99 | 84 (R) |
| 12 | C 1 | >99 | 48 (R) |

TABLE 5

Hydrogenation of (E)-geranylacetone in dichloromethane: Comparison of the reactivities of Ir-complex B 1 with different anion

| Example | Catalyst | Anion Y | Amount of catalyst [mol %] | Time [hours] | Yield of product [%] |
|---|---|---|---|---|---|
| 13 | B 1 | BAr$_F$ | 1.0 | 2 | >99 |
| 14 | B 1 | BAr$_F$ | 0.5 | 2 | 98 |
| 15 | B 1 | BAr$_F$ | 0.5 | 24 | 99 |
| 16 | B 1 | BAr$_F$ | 0.4 | 24 | 87 |
| 17 | B 1 | BAr$_F$ | 0.3 | 24 | 11 |
| 18 | B 1a | Al(OC(CF$_3$)$_3$)$_4$ | 1.0 | 2 | >99 |
| 19 | B 1a | Al(OC(CF$_3$)$_3$)$_4$ | 0.5 | 2 | 35 |
| 20 | B 1a | Al(OC(CF$_3$)$_3$)$_4$ | 0.5 | 24 | 49 |
| 21 | B 1a | Al(OC(CF$_3$)$_3$)$_4$ | 0.4 | 24 | 24 |

TABLE 6

Hydrogenation of (E)-geranylacetone in dichloromethane: Optimization of the reaction conditions.

| Example | Catalyst | Anion | Amount of catalyst [mol %] | Time [hours] | Yield of product [%] |
|---|---|---|---|---|---|
| 22 | B 1 | BAr$_F$ | 1.0 | 24 | >99 |
| 23 | B 1 | BAr$_F$ | 0.5 | 24 | >99 |
| 24 | B 1 | BAr$_F$ | 0.4 | 24 | >99 |
| 25 | B 1 | BAr$_F$ | 0.3 | 24 | 30 |

Examples 26 to 33

Preparation of 3,7,11-Trimethyldodecan-1-ol

The hydrogenation was carried out according to procedure 1, whereby 55.6 mg (0.25 mmol) of (2E,6E)-farnesol [=(2E,6E)-3,7,11-Trimethyldodeca-2,6,10-trien-1-ol] and 1 mol-% of Ir catalyst were used.

$^1$H-NMR (400.1 MHz, CDCl$_3$) of the product: δ=0.84 (d, $^3$J=6.8 Hz, 3 H, *CH—CH$_3$), 0.86 (d, $^3$J=6.8 Hz, 6 H, CH(CH$_3$)$_2$), 0.89 (d, $^3$J=6.6 Hz, 3 H, *CH—CH$_3$), 1.0-1.42 (m, 14 H, 6 CH$_2$, 2 CH), 1.55 (m, 3 H, CH$_2$, CH), 3.68 (m, 2 H, CH$_2$—OH).—GC: Restek Rtx-1701, 60 kPa He, temperature program: 50° C. (0 min), 10° C./min, 250° C. (10 min); solvent: n-heptane; t$_R$ [3,7,11-trimethyldodecane-1-ol]=18.5 min, t$_R$ [IIb]=19.8 min.

The results are presented in the following table 7:

| | Example | | | | | | | |
|---|---|---|---|---|---|---|---|---|
| | 26 | 27 | 28 | 29 | 30 | 31 | 32 | 33 |
| | Catalyst | | | | | | | |
| | A 2 | A 4 | A 5a) | B 1 | C 1 | C 4 | E 1 | F 1b) |
| 3S,7S [%] | 50 | 37 | 34 | 72 | 42 | 43 | 79 | 52 |
| 3R,7R [%] | 5 | 13 | 15 | 1 | 10 | 8 | 0.5 | 2 |
| 3S,7R [%] | 38 | 36 | 33 | 23 | 11 | 8 | 13.5 | 38 |
| 3R,7S [%] | 7 | 14 | 18 | 4 | 37 | 41 | 7 | 8 |
| ee (3S) [%] | 77 | 46 | 35 | 90 | 6 | 2 | 85 | 80 |
| ee (7S) [%] | 14 | 2 | 4 | 53 | 58 | 68 | 72 | 19 |

The term "ee (3S)" denotes a value which is calculated for quantifying the extent of enantiomeric purity at C-3, omitting stereochemical information on C-7 as follows: ee (3S)=[(3S7R+3S7S) minus (3R7S+3R7R)] divided by [sum of all four stereoisomers (3S7R+3S7S+3R7S+3R7R)].

The term "ee (7S)" denotes a value which is calculated for quantifying the extent of enantiomeric purity at C-7, omitting stereochemical information on C-3 as follows: ee (7S)=[(3S7S+3R7S) minus (3R7R+3S7R)] divided by [sum of all four stereoisomers (3S7S+3R7S+3R7R+3S7R)].

Examples 34 to 39

Preparation of 3,7,11-Trimethyl-Dodecanoic Acid Ethyl Ester

The hydrogenation was carried out according to procedure 1, whereby 66.1 mg (0.25 mmol) of (2E,6E)-farnesene acid ethyl ester [=(2E,6E)-3,7,11-trimethyl-dodeca-2,6,10-triene acid ethyl ester] and 1 mol-% of the Ir-catalyst were used.

$^1$H-NMR (400.1 MHz, CDCl$_3$): δ=0.84 (d, $^3$J=6.6 Hz, 3 H, *CH—CH$_3$), 0.86 (d, $^3$J=6.6 Hz, 6 H, CH(CH$_3$)$_2$), 0.93 (d, $^3$J=6.6 Hz, 3 H, *CH—CH$_3$), 1.0-1.4 (m, 13 H, 6 CH$_2$, CH(CH$_3$)$_2$), 1.25 (t, $^3$J=7.0 Hz, 3 H, O—CH$_2$—CH$_3$), 1.52 (m, 1 H, *CH), 1.94 (m, 1 H, *CH), 2.07 (ddt, $^2$J=14.7 Hz, $^3$J=8.1 Hz, $^4$J=1.5 Hz, 1 H, CH$_2$—COOEt), 2.28 (ddt, $^2$J=14.7 Hz, $^3$J=6.1 Hz, $^4$J=1.8 Hz, 1 H, CH$_2$—COOEt), 4.13 (q, $^3$J=7.0 Hz, 2 H, O—CH$_2$—CH$_3$).—GC: Restek Rtx-1701, 60 kPa He, temperature program: 50° C. (0 min), 10° C./min, 250° C. (10 min); solvent: n-heptane; t$_R$ [Ic]=19.1 min, t$_R$ [IIc]=21.0 min.

The results are presented in the following table 8:

| | Example | | | | | |
|---|---|---|---|---|---|---|
| | 34 | 35 | 36 | 37 | 38 | 39 |
| | Catalyst | | | | | |
| | A 2 | A 4 | B 1 | B 2 | C 5 | E 1 |
| 3S,7S [%] | 50 | 36 | 70 | 36 | 24 | 57 |
| 3R,7R [%] | 6 | 11 | 2 | 5 | 24 | 6 |
| 3S,7R [%] | 36 | 42 | 20 | 52 | 14 | 20 |
| 3R,7S [%] | 8 | 11 | 8 | 7 | 38 | 17 |
| ee C-3 [%] | 71 (S) | 57 (S) | 80 (S) | 76 (S) | 24 (R) | 54 (S) |
| ee C-7 [%] | 16 (S) | 6 (S) | 56 (S) | 13 (R) | 25 (S) | 49 (S) |

The term "ee C-3 (S)" denotes a value which is calculated for quantifying the extent of enantiomeric purity at C-3, omitting stereochemical information on C-7 as follows: ee C-3 (S)=[(3S7R+3S7S) minus (3R7S+3R7R)] divided by [sum of all four stereoisomers (3S7R+3S7S+3R7S+3R7R)].

The term "ee C-3 (R)" denotes a value which is calculated for quantifying the extent of enantiomeric purity at C-3, omitting stereochemical information on C-7 as follows: ee C-3 (R)=[(3R7R+3R7S) minus (3S7S+3S7R)] divided by [sum of all four stereoisomers (3R7R+3R7S+3S7S+3S7R)].

The term "ee C-7 (S)" denotes a value which is calculated for quantifying the extent of enantiomeric purity at C-7, omitting stereochemical information on C-3 as follows: ee C-7 (S)=[(3S7S+3R7S) minus (3R7R+3S7R)] divided by [sum of all four stereoisomers (3S7S+3R7S+3R7R+3S7R)].

The term "ee C-7 (R)" denotes a value which is calculated for quantifying the extent of enantiomeric purity at C-7, omitting stereochemical information on C-3 as follows: ee C-7 (R)=[(3S7R+3R7R) minus (3R7S+3S7S)] divided by [sum of all four stereoisomers (3S7R+3R7R+3R7S+3S7S)].

Procedure 2: Converting an Ester such as 3,7,11-Trimethyl-dodecanoic Acid Ethyl Ester into a Derivative for Determination of the Stereoisomeric Composition 0.25 mmol of the isolated ester were dissolved in 2 ml of absolute tetrahydrofuran and mixed with 66 mg (1.75 mmol, 7 mol equivalents) of LiAlH$_4$. The grey suspension was stirred for one hour at room temperature. Afterwards 5 ml of destillated water were added under ice cooling and stirring was continued for another 10 minutes. The resulting phases were separated and the aqueous phase was extracted twice with diethyl ether. The combined organic extracts were dried over MgSO$_4$ and the solvent was removed. The isolated alcohol, e.g., 3,7,11-trimethyldodecan-1-ol was further reacted to the corresponding aldehyde, e.g., 3,7,11-trimethyl-dodecanal without any purification.

Oxidation of 3,7,11-Trimethyldodecane-1-ol to 3,7,11-Trimethyl-dodecanal

The isolated alcohol was dissolved under Ar atmosphere in 1 ml of absolute dichloromethane. 60 mg of pyridinium chlorochromate were added. The brown suspension was stirred until the turn-over was complete (ca. 3 hours) at room temperature. Then the suspension was diluted with 3 ml of diethyl ether and filtrated. The solvent was removed and the raw product purified by column chromatography on silica gel (solvent: diethyl ether). The solvent was removed. Thin layer chromatography: starting material: R$_f$-value=0.22; product: R$_f$-value=0.67 (SiO$_2$, n-hexane/ethyl acetate (9:1); development with basic KMnO$_4$ solution). For the preparation of the corresponding acetal the raw aldehyde was immediately further reacted.

$^1$H-NMR (400.1 MHz, CDCl$_3$): δ=0.84 (d, $^3$J=6.6 Hz, 3 H, *CH—CH$_3$), 0.86 (d, $^3$J=6.6 Hz, 6 H, CH(CH$_3$)$_2$), 0.97 (d, $^3$J=6.6 Hz, 3 H, *CH—CH$_3$), 1.02-1.42 (m, 13 H, 6 CH$_2$,

CH), 1.52 (m, 1 H, *CH), 1.96 (m, 1 H, *CH), 2.14 (ddd, $^2J$=14.9 Hz, $^3J$=5.8 Hz, $^3J$=2.0 Hz, 1 H, —CH$_2$—CHO), 2.35 (ddd, $^2J$=14.9 Hz, $^3J$=8.1 Hz, $^3J$=2.0 Hz, 1 H, —CH$_2$—CHO), 9.75 (t, $^3J$=2.3 Hz, 1 H, CHO).

Acetalisation of 6,10-Dimethylundecane-2-One to Di-(2-Methyl-Ethyl)-(4R,5R)-2-[4,8-Dimethylnonyl]-2-Methyl-1,3-Dioxolane-4,5-Dicarboxylate To 0.25 mmol of (6R)-6,10-dimethylundecane-2-one and (6S)-6,10-dimethylundecane-2-one, respectively, were added 142 mg (0.38 mmol, 1.5 mol equivalents) of (2R,6R)-bissilylether (L-3) in 1 ml of absolute dichloromethane under Ar atmosphere. The reaction mixture was cooled to −78° C. At this temperature 20 μL (0.1 mmol, 0.4 mol equivalents) of trimethylsilyl triflate were added. After 15 minutes the cooling bath was removed and the reaction mixture stirred for 12 hours at room temperature. Afterwards 0.14 ml (1.0 mmol) of triethyl amine were added and stirring continued for further 10 minutes. Then the solvents were removed in high vacuum. The residue was dissolved in diethyl ether, filtered over silica gel and the solvent evaporated. For determination of the diastereomeric excess the raw product was analyzed via GC without any further purification.

TLC: R$_f$-value=0.27 (SiO$_2$, n-hexane/ethyl acetate 9:1); R$_f$-value (Ia)=0.32.—GC: achiral column: CP-Sil-88 (50 m, 0.25 mm, 0.25 μm), 100% cyanopropylpolysiloxan; carrier gas: hydrogen (90 kPa); split injector (1:30), injection temperature: 250° C.; FID detector, detection temperature: 250° C.; temperature program: 147° C. (isotherm); Solvent: dichloromethane; t$_R$ (4R,5R,4'S-acetal)=129.3 min, t$_R$ (4R,5R,4'R-acetal)=130.7 min.

$^1$H-NMR (400.1 MHz, CDCl$_3$): δ=0.84 (d, $^3J$=6.6 Hz, 3 H, *CH—CH$_3$), 0.85 (d, $^3J$=6.6 Hz, 6 H, CH(CH$_3$)$_2$), 1.00-1.57 (m, 12 H, 6 CH$_2$), 1.29 (d, $^3J$=6.3 Hz, 12 H, CO$_2$CH(CH$_3$)$_2$), 1.44 (s, 3 H, acetal-CH$_3$), 1.69 (m, 2 H, CH), 4.63 (d, $^3J$=6.3 Hz, 1 H, *CH (tartrate), 4.67 (d, $^3J$=6.3 Hz, 1 H, *CH (tartrate)), 5.13 (sept., $^3J$=6.3 Hz, 2 H, 2 CO$_2$CH(CH$_3$)$_2$).—

Acetalisation of 3,7,11-Trimethyl-Dodecane-1-Carbaldehyde to di-(2-Methylethyl)-(4R,5R/4S,5S)-[2,6,10-Trimethylundecyl]-1,3-di-Oxolan-4,5-Dicarboxylate To 71 mg L-3 and D-3, respectively, were added under Ar atmosphere 0.5 ml of a solution of 0.25 mmol of freshly prepared 3,7,11-trimethyl-dodecane-1-carbaldehyde and 1.0 ml of absolute dichloromethane. The reaction mixture was cooled to −78° C. At this temperature 10 μL (0.05 mmol, 0.4 mol equivalents) of trimethylsilyl triflate were added dropwise. The further proceeding corresponds to the proceeding described above for the preparation of acetal of 6,10-dimethylundecane-2-one.

TLC: R$_f$-value (product)=0.25 (SiO$_2$, n-hexane/ethyl acetate 9:1); R$_f$-value (starting material)=0.45.—GC: achiral column: CP-Sil-88 (50 m, 0.25 mm, 0.25 μm), 100% cyanopropylpolysiloxan; carrier gas: hydrogen (90 kPa), split injector (1:30), injection temperature: 250° C., FID detector, detection temperature: 250° C.; temperature program: 110° C.→200° C. with a heating rate of 0.5° C./min; t$_R$ (L-2'S,6'R-acetal)=144.3 min, t$_R$ {(L-2'R,6'S-acetal)+(L-2'S,6'S-acetal)}=145.0 min, t$_R$ (L-2'R,6'R-acetal)=145.6 min, or t$_R$ (D-2'R,6'S-acetal)=144.3 min, t$_R$ {(D-2'S,6'R-acetal)+(D-2'R,6'R-acetal)}=145.0 min, t$_R$ (D-2'S,6'S-acetal)=145.6 min.

$^1$H-NMR (400.1 MHz, CDCl$_3$): δ=0.83 (d, $^3J$=6.6 Hz, 3 H, *CH—CH$_3$), 0.86 (d, $^3J$=6.8 Hz, 6 H, CH(CH$_3$)$_2$), 0.94 (d, $^3J$=6.6 Hz, 3 H, *CH—CH$_3$), 1.00-1.65 (m, 16 H, 7×CH$_2$, 2×*CH), 1.28 (d, $^3J$=6.3 Hz, 12 H, 2 CO$_2$CH(CH$_3$)$_2$), 4.56 (d, $^3J$=4.3 Hz, 1 H, *CH (tartrate), 4.65 (d, $^3J$=4.3 Hz, 1 H, *CH (tartrate), 5.11 (sept., $^3J$=6.3 Hz, 1 H, CO$_2$CH(CH$_3$)$_2$), 5.12 (sept., $^3J$=6.3 Hz, 1 H, CO$_2$CH(CH$_3$)$_2$), 5.30 (t, $^3J$=5.05 Hz, 1 H, acetal-H).—

Examples 40 to 68

Hydrogenation of Tocotrienyl Acetates

Stereoselective Hydrogenation of (2R)- and (2S)-α-Tocotrienyl Acetate, as well as of (2R)- and (2S)-γ-Tocotrienyl Acetate Examples 40 to 61

Preparation of (2R)-α-Tocopheryl Acetate and (2S)-α-Tocopheryl Acetate

Hydrogenation according to procedure 1, whereby 23.4 mg (0.05 mmol) of starting material and 1 mol-% of Ir catalyst (based on the amount of starting material) in 0.5 ml of absolute dichloromethane were used. Used starting materials: (2R,3'E,7'E)-α-tocotrienyl acetate, (2S,3'E,7'E)-α-tocotrienyl acetate.

Determination of the turn-over via $^1$H-NMR; (2R/2S,3'E,7'E)-α-tocotrienyl acetate: 5.13 (m, 3 H, 3 alken-CH).—$^1$H-NMR (400.1 MHz, CD$_2$Cl$_2$): δ=0.87 (d, $^3J$=6.6 Hz, 3 H, *CH—CH$_3$), 0.88 (d, $^3J$=6.6 Hz, 3 H, *CH—CH$_3$), 0.89 (d, $^3J$=6.6 Hz, 6 H, CH(CH$_3$)$_2$), 1.06-1.63 (m, 21 H, 9 CH$_2$, 3 CH), 1.26 (s, 3 H, O—*C—CH$_3$), 1.82 (m, 2 H, O—*C—CH$_2$), 1.97 (s, 3 H, Ph—CH$_3$), 2.01 (s, 3 H, Ph—CH$_3$), 2.10 (s, 3 H, Ph—CH$_3$), 2.31 (OC(O)CH$_3$), 2.62 (m, 2 H, CH$_2$ (cycl.)).

The results are presented in the following tables 9, 10, 11 and 12:

TABLE 9

Hydrogenation of (2S,3'E,7'E)-α-tocotrienyl acetate

| Example | catalyst | 2S,4'S,8'S [%] | 2S,4'R,8'R [%] | 2S,4'S,8'R [%] | 2S,4'R,8'S [%] | "ee" (C 4') [%] | "ee" (C 8') [%] |
|---|---|---|---|---|---|---|---|
| 40 | D 1 | 48 | 10 | 18 | 24 | 31 (S) | 43 (S) |
| 41 | E 1 | 53 | 8 | 19 | 20 | 44 (S) | 48 (S) |
| 42 | G 1 | 20 | 31 | 21 | 28 | 19 (R) | 4 (R) |

TABLE 10

Hydrogenation of (2R,3'E,7'E)-α-tocotrienyl acetate

| Example | Catalyst | 2R,4'R,8'R [%] | 2R,4'S,8'S [%] | 2R,4'R,8'S [%] | 2R,4'S,8'R [%] | "ee" (C 4') [%] | "ee" (C 8') [%] |
|---|---|---|---|---|---|---|---|
| 43 | B 1 | 18 | 32 | 17 | 33 | 29 (S) | 2 (S) |
| 44 | D 1 | 9 | 49 | 22 | 20 | 39 (S) | 43 (S) |
| 45 | E 1 | 6 | 58 | 18 | 18 | 51 (S) | 51 (S) |
| 46 | E 2 | 55 | 8 | 17 | 20 | 45 (R) | 51 (R) |
| 47 | E 7 | 2 | 71 | 13 | 14 | 70 (S) | 67 (S) |

TABLE 11

Hydrogenation of (2S,3'E,7'E)-α-tocotrienyl acetate

| Example | Catalyst | 2S,4'S,8'S [%] | 2S,4'R,8'R [%] | 2S,4'S,8'R [%] | 2S,4'R,8'S [%] | "ee" (C 4') [%] | "ee" (C 8') [%] |
|---|---|---|---|---|---|---|---|
| 48 | E 1 | 53 | 8 | 19 | 20 | 46 (S) | 46 (S) |
| 49 | E 3 | 68 | 3 | 16 | 13 | 67 (S) | 62 (S) |
| 50 | E 4 | 66 | 5 | 15 | 14 | 62 (S) | 61 (S) |
| 51 | E 5 | 53 | 8 | 19 | 20 | 46 (S) | 46 (S) |
| 52 | E 6 | 72 | 2 | 14 | 12 | 72 (S) | 68 (S) |
| 53 | E 7 | 57 | 6 | 19 | 18 | 52 (S) | 50 (S) |
| 54 | E 8 | 67 | 4 | 15 | 14 | 64 (S) | 62 (S) |
| 55 | E 9 | 74 | 3 | 12 | 11 | 72 (S) | 71 (S) |
| 56 | E 10 | 68 | 4 | 15 | 13 | 66 (S) | 64 (S) |
| 57 | E 11 | 68 | 3 | 15 | 14 | 66 (S) | 65 (S) |
| 58 | E 12 | 76 | 2 | 12 | 10 | 75 (S) | 72 (S) |
| 59 | E 13 | 87 | 2 | 6 | 5 | 87 (S) | 83 (S) |
| 60 | E 14 | 90 | 1 | 5 | 4 | 90 (S) | 88 (S) |

If the catalyst E15 (enantiomer to Ir complex E14) was used (2R,3'E,7'E)-α-tocotrienyl acetate was hydrogenated to (2R,4'R,8'R)-tocopheryl acetate in a yield of 90% (see table 12).

TABLE 12

Hydrogenation of (2R,3'E,7'E)-α-tocotrienyl acetate

| Example | Catalyst | 2R,4'R,8'R [%] | 2R,4'S,8'S [%] | 2R,4'R,8'S [%] | 2R,4'S,8'R [%] | "ee" (C 4') [%] | "ee" (C 8') [%] |
|---|---|---|---|---|---|---|---|
| 61 | E 15 | 90 | 1 | 5 | 4 | 90 (R) | 88 (R) |

Examples 62 to 68

(2R)-γ-Tocopheryl Acetate and (2S)-γ-Tocopheryl Acetate

Hydrogenation according to procedure 1, whereby 0.05 mmol (22.7 mg) of the starting material and 1 mol-% (based on the amount of starting material) of the Ir catalyst in 0.5 ml of absolute dichloromethane were used. Used starting materials: (2R,3'E,7'E)-γ-tocotrienyl acetate, (2S,3'E,7'E)-γ-tocotrienyl acetate.

The conversion was determined via $^1$H-NMR; (2R/2S,3'E,7'E)-γ-tocotrienyl acetate: 5.13 (m, 3 H, 3 Alken-CH). $^1$H-NMR (400.1 MHz, CD$_2$Cl$_2$): δ=0.86 (d, $^3$J=6.6 Hz, 3 H, *CH—CH$_3$), 0.87 (d, $^3$J=6.6 Hz, 6 H, CH(CH$_3$)$_2$), 0.88 (d, $^3$J=6.6 Hz, 3 H, *CH—CH$_3$), 1.02-1.68 (m, 21 H, 9 CH$_2$, 3 CH), 1.28 (s, 3 H, O—*C—CH$_3$), 1.76 (dt, $^2$J=13.5 Hz, $^3$J=6.6 Hz, 1 H, O—*C—CH$_2$), 1.80 (dt, $^2$J=13.5 Hz, $^3$J=6.6 Hz, 1 H, O—*C—CH$_2$), 2.01 (s, 3 H, Ph—CH$_3$), 2.12 (s, 3 H, Ph—CH$_3$), 2.27 (s, 3 H, OC(O)CH$_3$), 2.72 (m, 2 H, CH$_2$ (cycl.), 6.56 (s, 1 H, ar. CH).

The results are presented in the following tables 13 and 14:

TABLE 13

Hydrogenation of (2S,3'E,7'E)-γ-tocotrienyl acetate

| Example | Catalyst | 2S,4'S,8'S [%] | 2S,4'R,8'R [%] | 2S,4'S,8'R [%] | 2S,4'R,8'S [%] | "ee" (C 4') [%] | "ee" (C 8') [%] |
|---|---|---|---|---|---|---|---|
| 62 | B 1 | 24 | 25 | 24 | 27 | 3 (R) | 2 (S) |

TABLE 14

Hydrogenation of (2R,3'E,7'E)-γ-tocotrienyl acetate
a) 4 mol % of the Ir-catalyst were used.

| Example | catalyst | 2R,4'R,8'R [%] | 2R,4'S,8'S [%] | 2R,4'R,8'S [%] | 2R,4'S,8'R [%] | "ee" (C 4') [%] | "ee" (C 8') [%] |
|---------|----------|---------------|---------------|---------------|---------------|----------------|----------------|
| 63 | A 2 | 12 | 43 | 23 | 22 | 30 (S) | 31 (S) |
| 64 | C 1 | 8 | 51 | 20 | 21 | 43 (S) | 41 (S) |
| 65 | D 1 | 8 | 52 | 21 | 19 | 41 (S) | 46 (S) |
| 66 | E 1 | 8 | 53 | 20 | 19 | 44 (S) | 48 (S) |
| 67 | F 1a) | 46 | 12 | 21 | 21 | 34 (R) | 35 (R) |
| 68 | H 1 | >98 | <0.5 | <0.5 | <0.5 | >98 (R) | >98 (R) |

For determination of the stereoisomeric composition the tocopheryl acetates were converted into tocopherols and tocopherol methyl ethers as follows:

Reduction of the Tocopheryl Acetates to the Corresponding Tocopherols

Preparation of (2R)-α-Tocopherol and (2S)-α-Tocopherol

Synthesis according to procedure 2, whereby 23.7 mg (0.05 mmol) of the starting material and 13 mg (0.35 mmol) of LiAlH$_4$ were used in 1 ml of absolute tetrahydrofuran. Used starting materials: (2R)-α-tocopheryl acetate and (2S)-α-tocopheryl acetate.

$^1$H-NMR (400.1 MHz, CD$_2$Cl$_2$): δ=0.86 (d, $^3$J=6.6 Hz, 3 H, *CH—CH$_3$), 0.87 (d, $^3$J=6.6 Hz, 3 H, *CH—CH$_3$), 0.88 (d, $^3$J=6.6 Hz, 6 H, CH(CH$_3$)$_2$), 1.02-1.63 (m, 21 H, 9 CH$_2$, 3 CH), 1.23 (s, 3 H, O—*C—CH$_3$), 1.79 (m, 2 H, O—*C—CH$_2$), 2.10 (br s, 6 H, 2 Ph—CH$_3$), 2.14 (s, 3 H, Ph—CH$_3$), 2.60 (m, 2 H, CH$_2$ (cycl.)), 4.28 (br s, 1 H, OH).

Preparation of (2R)-γ-Tocopherol and (2S)-γ-Tocopherol

Synthesis according to procedure 2, whereby 22.9 mg (0.05 mmol) of starting material and 13 mg (0.35 mmol) of LiAlH$_4$ were used in 1 ml of absolute tetrahydrofuran. Used starting materials: (2R)-γ-tocopheryl acetate and (2S)-γ-tocopheryl acetate.

$^1$H-NMR (400.1 MHz, CD$_2$Cl$_2$): δ=0.86 (d, $^3$J=6.6 Hz, 3 H, *CH—CH$_3$), 0.87 (d, $^3$J=6.6 Hz, 3 H, *CH—CH$_3$), 0.88 (d, $^3$J=6.6 Hz, 6 H, CH(CH$_3$)$_2$), 1.04-1.63 (m, 21 H, 9 CH$_2$, 3 CH), 1.28 (s, 3 H, O—*C—CH$_3$), 1.75 (m, 2 H, O—*C—CH$_2$), 2.09 (s, 3 H, Ph—CH$_3$), 2.11 (s, 3 H, Ph—CH$_3$), 2.67 (m, 2 H, CH$_2$ (cycl.), 4.35 (br s, 1 H, OH), 6.36 (s, 1 H, ar. CH).

Procedure 3

Preparation of the Methyl Ether of α- and γ-Tocopherol 0.25 mmol of the isolated α- or γ-tocopherol (raw product) were dissolved under an Ar atmosphere in 1 ml of absolute dimethoxyethan. 0.2 ml (2.5 mmol) of a 50 weight-% aqueous KOH solution were added dropwise. After stirring for 10 minutes 0.12 ml (1.25 mmol) of dimethyl sulfate were added dropwise. Afterwards the reaction mixture was stirred for one hour at room temperature. After complete turn-over the solvent was evaporated. The residue was stirred in 5 ml of distilled water and 10 ml of n-hexane for 5 minutes. The organic and the aqueous phase were separated. The aqueous phase was extracted with 10 ml of n-hexane. The combined organic phases were dried over MgSO$_4$ and the solvent evaporated. The obtained raw product was analyzed without any further purification via GC to determine the ratio of the diastereomers.

Preparation of (2R)-α-Tocopheryl Methyl Ether and (2S)-α-Tocopheryl Methyl Ether Synthesis according to procedure 3; GC: achiral column: CP-Sil-88 (50 m, 0.25 mm, 0.25 μm), 100% cyanopropylpolysiloxane; carrier gas: hydrogen (90 kPa); split injector (1:30), injection temperature: 280° C.; FID detector, detection temperature: 250° C.; temperature program: 170° C. (isotherm); solvent: ethyl acetate; t$_R$ of the products: t$_R$ (2R,4'R,8'S)=144.5 min, t$_R$ (2R,4'R,8'R)=146.2 min, t$_R$ (2R,4S,8R)=148.4 min, t$_R$ (2R,4'S,8'S) =150.8 min bzw. t$_R$ (2S,4'S,8'R)=144.5 min, t$_R$ (2S,4'S,8'S)=146.2 min, t$_R$ (2S,4'R,8'S)=148.4 min, t$_R$ (2S,4'R,8'R)=150.8 min.

$^1$H-NMR (400.1 MHz, CD$_2$Cl$_2$): δ=0.86 (d, $^3$J=6.6 Hz, 3 H, *CH—CH$_3$), 0.87 (d, $^3$J=6.6 Hz, 3 H, *CH—CH$_3$), 0.88 (d, $^3$J=6.6 Hz, 6 H, CH(CH$_3$)$_2$), 1.03-1.65 (m, 21 H, 9 CH$_2$, 3 CH), 1.25 (s, 3 H, O—*C—CH$_3$), 1.75 (m, 2 H, O—*C—CH$_2$), 2.09 (br s, 9 H, 3 Ph—CH$_3$), 2.72 (m, 2 H, CH$_2$ (cycl.), 3.74 (s, 3 H, —O—CH$_3$).

Preparation of (2R)-γ-Tocopheryl Methyl Ether and (2S)-γ-Tocopheryl Methyl Ether Preparation according to procedure 3; GC: achiral column: CP-Sil-88 (50 m, 0.25 mm, 0.25 μm), 100% cyanopropylpolysiloxane; carrier gas: hydrogen (90 kPa); split injector (1:30), injection temperature: 280° C.; FID detector, detection temperature: 250° C.; temperature program: 170° C. (isotherm); solvent: ethyl acetate; t$_R$ of the products: t$_R$ (2R,4'R,8'S)=126.0 min, t$_R$ (2R,4'R,8'R)=127.5 min, t$_R$ (2R,4'S,8'R)=129.5 min, t$_R$ (2R,4'S,8'S)=132.0 min; and t$_R$ (2S,4'S,8'R)=126.0 min, t$_R$ (2S,4'S,8'S)=127.5 min, t$_R$ (2S,4'R,8'S)=129.5 min, t$_R$ (2S,4'R,8'R)=132.0 min.

$^1$H-NMR (400.1 MHz, CD$_2$Cl$_2$): δ=0.87 (d, $^3$J=6.6 Hz, 3 H, *CH—CH$_3$), 0.88 (d, $^3$J=6.6 Hz, 3 H, *CH—CH$_3$), 0.89 (d, $^3$J=6.6 Hz, 6 H, CH(CH$_3$)$_2$), 1.03-1.65 (m, 21 H, 9 CH$_2$, 3 CH), 1.29 (s, 3 H, O—*C—CH$_3$), 1.77 (m, 2 H, O—*C—CH$_2$), 2.09 (s, 3 H, Ph—CH$_3$), 2.10 (s, 3 H, Ph—CH$_3$), 2.72 (m, 2 H, CH$_2$ (cycl.), 3.74 (s, 3 H, —O—CH$_3$), 6.43 (s, 1 H, ar. CH).

Example 68

(2R)-γ-Tocopheryl Acetate (2R,3'E,7'E)-γ-Tocotrienyl acetate (22.7 mg, 0.05 mmol), catalyst (5×10$^{-7}$ mol, 1 mol %) and dichloromethane (0.5 ml) were added under nitrogen to a 2 ml glass vial containing a magnetic stir bar and placed in an autoclave. The autoclave was pressurized to 50 bar with H$_2$ and the solution stirred at 700 rpm for 2 hours. The pressure was then carefully released and the reaction mixture concentrated under reduced pressure. Hexane (1 ml) was added and the mixture filtered through a 0.2 μm syringe filter. The hexane solution was then concentrated to give 23 mg (100%) of (2R)-γ-tocopheryl acetate (>98% 2R,4'R,8'R; <0.5% 2R,4'R,8'S; <0.5% 2R,4'S, 8'R; <0.5% 2R,4'S,8'S) as an oil.

The invention claimed is:

1. Process for the manufacture of a compound of the formula I

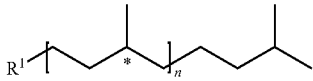
I wherein the position labelled with the asterisk is an asymmetry center and $R^1$ is a group of the formula

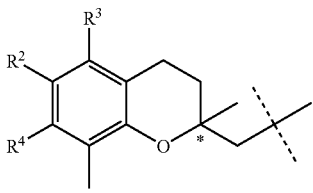

with $R^2$ being a hydroxyl group or a protected hydroxyl group, and $R^3$ and $R^4$ being independently from each other hydrogen or methyl, and n being an integer from 1 to 10, comprising the step of hydrogenating a compound of the formula II

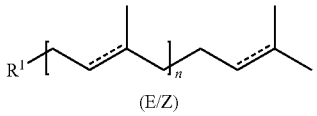
II
(E/Z)

wherein at least one carbon-carbon double bond is present, and wherein the dotted lines represent the possible positions of such (facultative) carbon-carbon double bonds; and $R^1$ and n are as above, in the presence of a chiral iridium (Ir) complex as the catalyst selected from the group consisting of Ir complexes of the formula III, IV, V, VI, VII, VIII, IX, X, XI or XV, and their enantioners of formula:

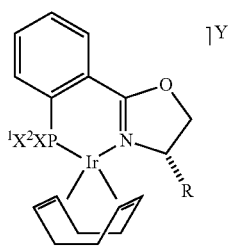
III

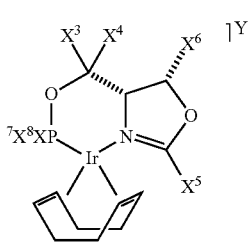
IV

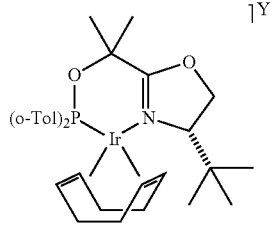
V

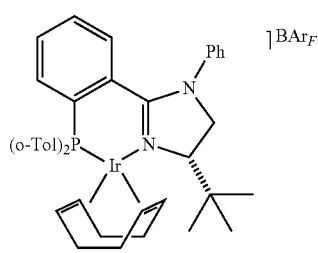
VI

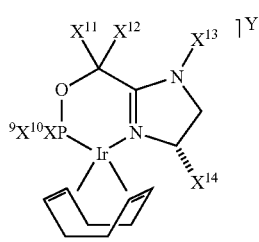
VII

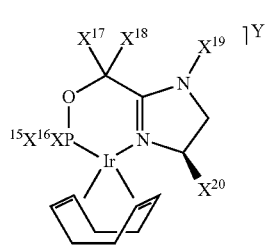
VIII

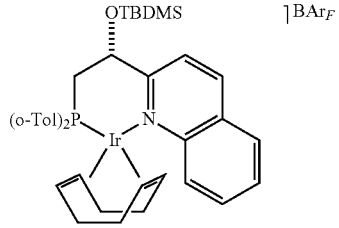
IX

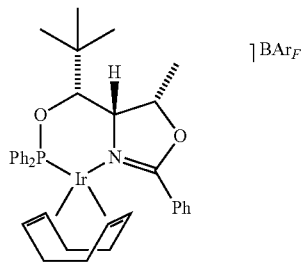
X

-continued

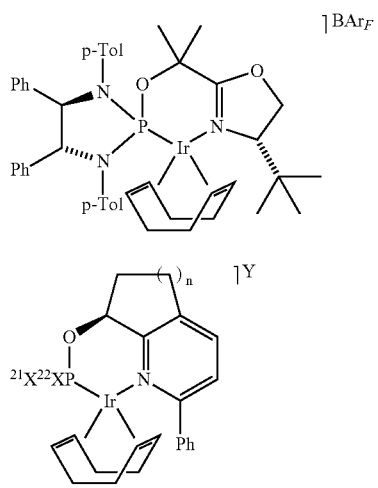

XI

XV wherein R, $X^1$, $X^2$, $X^3$, $X^4$, $X^5$, $X^6$, $X^7$, $X^8$, $X^9$, $X^{10}$, $X^{11}$, $X^{12}$, $X^{13}$, $X^{14}$, $X^{15}$, $X^{16}$, $X^{17}$, $X^{18}$, $X^{19}$, $X^{20}$, $X^{21}$ and $X^{22}$ are independently from each other hydrogen, $C_{1-4}$-alkyl, $C_{5-7}$-cycloalkyl, phenyl, phenyl substituted with one to three $C_{1-4}$-alkyl, $C_{1-4}$-alkoxy and/or $C_{1-4}$-perfluoroalkyl groups, benzyl, 1-naphthyl, or ferrocenyl, the anion Y is a weakly coordinating anion, n is 1 to 2, and "o-Tol" means ortho-tolyl, "Ph" means phenyl, "TBDMS" means tert-butyl-dimethylsilyl, "p-Tol" means para-tolyl, "$BAr_F$" means tetra(3,5-bis(trifluoromethyl)phenyl)borate, and the Ir complexes of the formula III to XI and XV, and the corresponding enantiomeric formula whereby the cyclooctadiene ligand is replaced by ethene or norbornadiene.

2. The process according to claim 1, wherein the compound of the formula II is a tocomonoenol, a tocodienol, or a tocotrienol which is hydrogenated to the corresponding compound of the formula I, wherein the tocomonoenol, the tocodienol, and the tocotrienol are of the formula XIII,

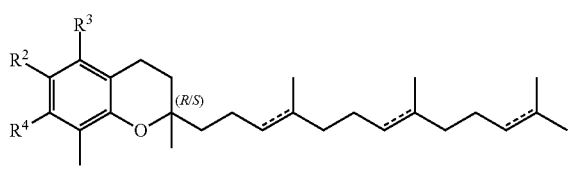

XIII wherein the dotted bonds are optional and at least one of the dotted bonds is present, and wherein $R^2$ is a hydroxyl group or a protected hydroxyl group and $R^3$ and $R^4$ are independently from each other hydrogen or methyl.

3. The process according to claim 1, wherein the amount of the catalyst is from about 0.05 to about 5 mol %, based on the amount of the compound of the formula II.

4. The process according to claim 1, wherein the compound of the formula II is selected from the group consisting of (2R,3'E,7'E)-α-tocotrienol, (2R,3'E,7'E)-β-tocotrienol, (2R,3'E,7'E)-γ-tocotrienol, (2R,3'E,7'E)-δ-tocotrienol, (2R,3'E,7'E)-α-tocotrienol methyl ether, (2R,3'E,7'E)-α-tocotrienol methoxymethylether, (2R,3'E,7'E)-α-tocotrienol methoxyethylether, (2R,3'E,7'E)-α-tocotrienol tetrahydropyranyl ether, (2R,3'E,7'E)-α-tocotrienol ethoxyethyl ether, (2R,3'E,7'E)-α-tocotrienol methoxyethoxyethyl ether, (2R,3'E,7'E)-α-tocotrienol acetic acid ester, (2R,3'E,7'E)-α-tocotrienol formic acid ester, (2R,3'E,7'E)-α-tocotrienol succinic acid monoester, (2R,3'E,7'E)-α-tocotrienol propionic acid ester, (2R,3'E,7'E)-α-tocotrienol benzoic acid ester, (2R,3'E,7'E)-α-tocotrienol palmitic acid ester, (2R,3'E,7'E)-β-tocotrienol methyl ether, (2R,3'E,7'E)-β-tocotrienol methoxymethylether, (2R,3'E,7'E)-β-tocotrienol methoxyethylether, (2R,3'E,7'E)-β-tocotrienol tetrahydropyranyl ether, (2R,3'E,7'E)-β-tocotrienol ethoxyethyl ether, (2R,3'E,7'E)-β-tocotrienol methoxyethoxyethyl ether, (2R,3'E,7'E)-β-tocotrienol acetic acid ester, (2R,3'E,7'E)-β-tocotrienol formic acid ester, (2R,3'E,7'E)-β-tocotrienol succinic acid monoester, (2R,3'E,7'E)-β-tocotrienol propionic acid ester, (2R,3'E,7'E)-β-tocotrienol benzoic acid ester, (2R,3'E,7'E)-β-tocotrienol palmitic acid ester, (2R,3'E,7'E)-γ-tocotrienol methyl ether, (2R,3'E,7'E)-γ-tocotrienol methoxymethylether, (2R,3'E,7'E)-γ-tocotrienol methoxyethylether, (2R,3'E,7'E)-γ-tocotrienol tetrahydropyranyl ether, (2R,3'E,7'E)-γ-tocotrienol ethoxyethyl ether, (2R,3'E,7'E)-γ-tocotrienol methoxyethoxyethyl ether, (2R,3'E,7'E)-γ-tocotrienol acetic acid ester, (2R,3'E,7'E)-γ-tocotrienol formic acid ester, (2R,3'E,7'E)-γ-tocotrienol succinic acid monoester, (2R,3'E,7'E)-γ-tocotrienol propionic acid ester, (2R,3'E,7'E)-γ-tocotrienol benzoic acid ester, (2R,3'E,7'E)-γ-tocotrienol palmitic acid ester, (2R,3'E,7'E)-δ-tocotrienol methyl ether, (2R,3'E,7'E)-δ-tocotrienol methoxymethylether, (2R,3'E,7'E)-δ-tocotrienol methoxyethylether, (2R,3'E,7'E)-δ-tocotrienol tetrahydropyranyl ether, (2R,3'E,7'E)-δ-tocotrienol ethoxyethyl ether, (2R,3'E,7'E)-δ-tocotrienol methoxyethoxyethyl ether, (2R,3'E,7'E)-δ-tocotrienol acetic acid ester, (2R,3'E,7'E)-δ-tocotrienol formic acid ester, (2R,3'E,7'E)-δ-tocotrienol succinic acid monoester, (2R,3'E,7'E)-δ-tocotrienol propionic acid ester, (2R,3'E,7'E)-δ-tocotrienol benzoic acid ester, (2R,3'E,7'E)-δ-tocotrienol palmitic acid ester, and mixtures thereof, as well as any part or extract of a plant oil containing at least a compound of said group.

5. Process according to claim 1, wherein the compound of the formula II is (2R,3'E,7'E)-α-tocotrienyl acetate, which is hydrogenated to a mixture of the four diastereoisomers (2R,4'S,8'R)-α-tocopheryl acetate, (2R,4'R,8'S)-α-tocopheryl acetate, (2R,4'R,8'R)-α-tocopheryl acetate and (2R,4'S,8'S)-α-tocopheryl acetate in the presence of the chiral Ir complex selected from the group consisting of Ir complexes of the formula E1, E2, E7, E15 and H1 and the enantioners thereof, wherein one diastereoisomer is manufactured in excess,

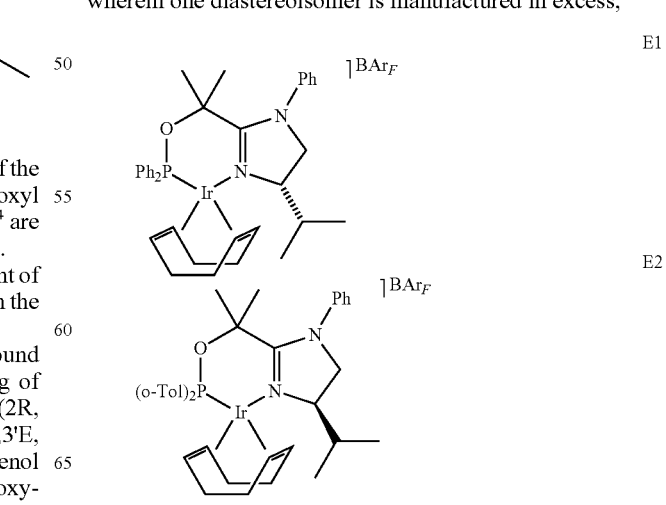

E1

E2

-continued

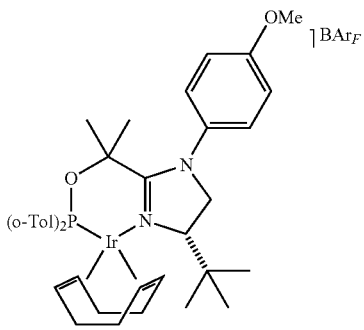
E7

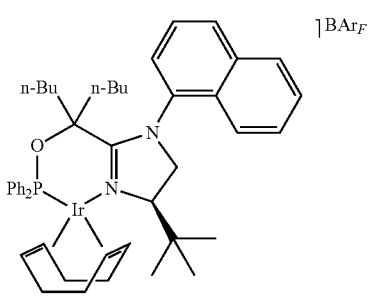
E15

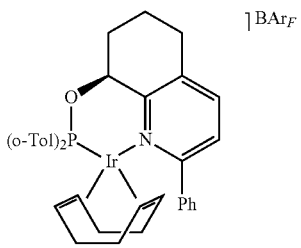
H1 and "o-Tol" means o-tolyl, "Ph" means phenyl, "BAr$_F$" is tetra(3,5-bis(trifluoromethyl)phenyl)borate, "n-Bu" means=n-butyl, and "Me" means methyl.

6. Process according to claim 1, wherein the compound of the formula II is (2R,3'E,7'E)-γ-tocotrienyl acetate which is hydrogenated to a mixture of the four diastereoisomers (2R,4'S,8'R)-γ-tocopheryl acetate, (2R,4'R,8'S)-γ-tocopheryl acetate, (2R,4'R,8'R)-γ-tocopheryl acetate and (2R,4'S,8'S)-γ-tocopheryl acetate in the presence of the chiral Ir complex C1, D1, E1, F1 or H1

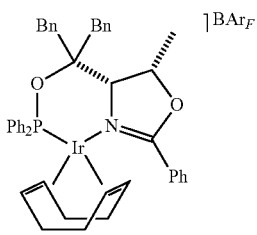
C1

-continued

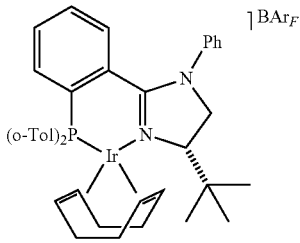
D1

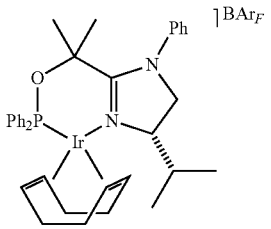
E1

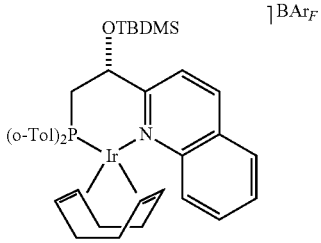
F1

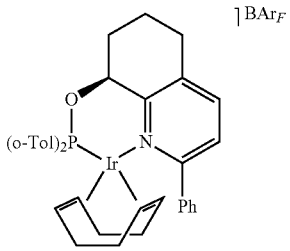
H1 whereby "Ph" means phenyl, "Bn" means benzyl, "BAr$_F$" is tetra(3,5-bis(trifluoromethyl)phenyl)borate[B(3,5-C$_6$H$_3$(CF$_3$)$_2$)$_4$]$^-$, "o-Tol" means o-tolyl, and "TBDMS" means tert-butyl-dimethyl silyl, as the catalyst, whereby one diastereoisomer is manufactured in excess.

7. A process for the manufacture of a hydrogenated part or extract of a plant oil, comprising the step of hydrogenating the part or extract of the plant oil comprising at least a tocotrienol of formula A

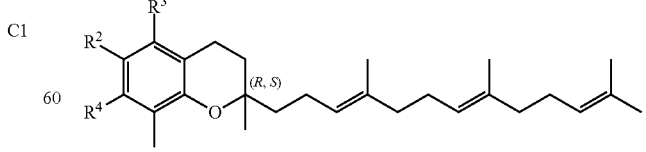
A in the presence of a chiral Ir complex as the catalyst with $R^2$ being a hydroxyl group or a protected hydroxyl group, and $R^3$ and $R^4$ being independently from each other hydrogen or methyl.

8. The process according to claim 7, wherein the tocotrienol of formula A is hydrogenated to a tocopherol of formula B

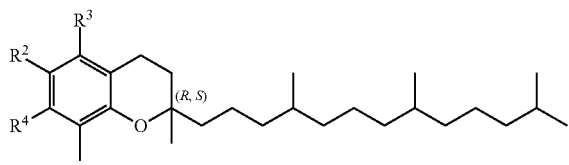

B with $R^2$ being a hydroxyl group or a protected hydroxyl group, and $R^3$ and $R^4$ being independently from each other hydrogen or methyl.

9. The process according to claim 7, wherein the chiral Ir complex is selected of the group consisting of Ir complexes of one of the formulae III to XI and XV and their corresponding enantiomers of formula:

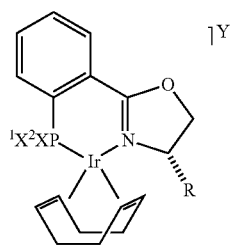

III

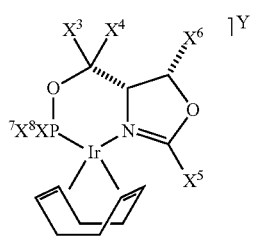

IV

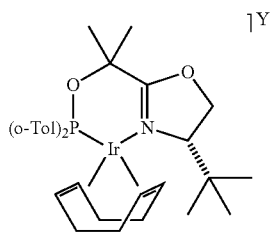

V

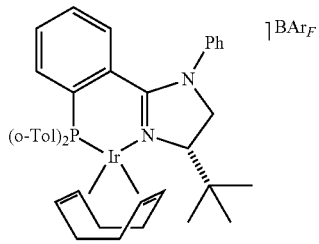

VI

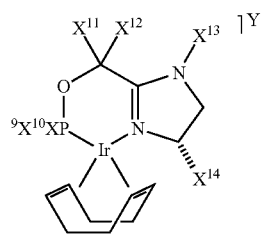

VII

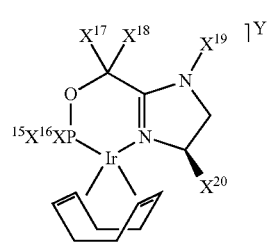

VIII

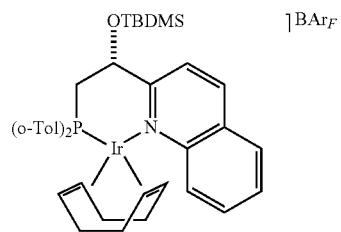

IX

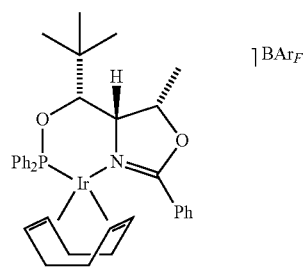

X

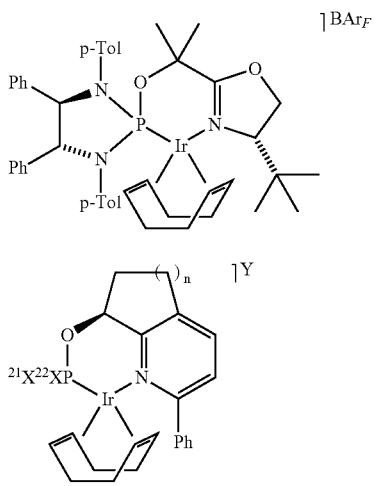

wherein R, $X^1, X^2, X^3, X^4, X^5, X^6, X^7, X^8, X^9, X^{10}, X^{11}, X^{12}, X^{13}, X^{14}, X^{15}, X^{16}, X^{17}, X^{18}, X^{19}, X^{20} X^{21}$ and $X^{22}$ are independently from each other hydrogen, $C_{1-4}$-alkyl, $C_{5-7}$-cycloalkyl, phenyl, phenyl substituted with one to three $C_{1-4}$-alkyl, $C_{1-4}$-alkoxy and/or $C_{1-4}$-perfluoroalkyl groups, benzyl, 1-naphthyl, or ferrocenyl, the anion Y is a weakly coordinating anion, n is 1 or 2, and "o-Tol" means ortho-tolyl, "Ph" means phenyl, "TBDMS" means tert-butyl-dimethylsilyl, "p-Tol" means para-tolyl, "BAr$_F$" means tetra(3,5-bis(trifluoromethyl)phenyl)borate or the Ir complex is of the formula III to XI or XV, or the corresponding enantiomeric formula whereby the cyclooctadiene ligand is replaced by ethene or norbornadiene.

10. The process according to claim 1, wherein n is 1-3.

11. The process according to claim 3, wherein the amount of catalyst is from about 0.09 to about 2.5 mol %.

12. The process according to claim 3, wherein the amount of catalyst is from about 0.1 to about 2.0 mol %.

13. The process according to claim 5, wherein the stereoisomer (2R,4'R,8'R)-α-tocopheryl acetate is at least 55%.

14. The process according to claim 5, wherein the stereoisomer (2R,4'R,8'R)-α-tocopheryl acetate is at least 90%.

15. The process according to claim 6, wherein the diastereoisomer is present in an amount of at least 45%.

16. The process according to claim 7, wherein the plant oil is palm oil.

* * * * *